US011986779B2

(12) United States Patent
Blumberg et al.

(10) Patent No.: US 11,986,779 B2
(45) Date of Patent: May 21, 2024

(54) RECRYSTALLIZED HI-6 DIMETHYLSULFATE

(71) Applicant: Southwest Research Institute, San Antonio, TX (US)

(72) Inventors: Shawn T. Blumberg, San Antonio, TX (US); Paul W. Miguel, San Antonio, TX (US)

(73) Assignee: SOUTHWEST RESEARCH INSTITUTE, San Antonio, TX (US)

( * ) Notice: Subject to any disclaimer, the term of this patent is extended or adjusted under 35 U.S.C. 154(b) by 46 days.

(21) Appl. No.: 16/949,666

(22) Filed: Nov. 10, 2020

(65) Prior Publication Data

US 2021/0138359 A1 May 13, 2021

Related U.S. Application Data

(60) Provisional application No. 62/933,814, filed on Nov. 11, 2019.

(51) Int. Cl.
B01D 9/00 (2006.01)
C07C 309/04 (2006.01)
C07D 213/81 (2006.01)

(52) U.S. Cl.
CPC .......... B01D 9/0054 (2013.01); C07C 309/04 (2013.01); C07D 213/81 (2013.01)

(58) Field of Classification Search
CPC .................................................. B01D 9/0054
See application file for complete search history.

(56) References Cited

U.S. PATENT DOCUMENTS

| 5,130,438 | A | 7/1992 | Hsiao et al. | |
| 2003/0152500 | A1* | 8/2003 | Dalziel | B01J 19/18 422/245.1 |
| 2004/0053928 | A1 | 3/2004 | Davies et al. | |
| 2006/0014749 | A1 | 1/2006 | Davies et al. | |
| 2010/0016604 | A1 | 1/2010 | Eddolls et al. | |

FOREIGN PATENT DOCUMENTS

| EP | 1886995 | | 2/2008 |
| SK | 288013 | B6 * | 6/2007 |
| WO | 9317007 | | 9/1993 |

OTHER PUBLICATIONS

Zubrick, James W. The Organic Chem Lab Survival Manual: A Student's Guide to Techniques 1988, Wiley: New York, pp. 103-106.*
Healy "Pharmaceutical solvates, hydrates and amorphous forms: A special emphasis on cocrystals" Advanced Drug Delivery Reviews (2017).*
Draft chapter for The International Pharmacopoeia 5 (Jul. 2017) on Polymorphism.*
Camarasu "Recent progress in the determination of volatile impurities in pharmaceuticals" Trends in Analytical Chemistry, vol. 25, No. 8, 2006 768-777.*
West, Anthony R., Solid State Chemistry and its Applications, Wiley, New York, 1988, pp. 358 & 365.*
Environmental Protection Agency (EPA). Bis(chloromethyl)ether (BCME), 1992, 4 pages. https://www.epa.gov/sites/production/filed/2016-09/documents/bis-chloromethyl-ether.pdf.
Peter Eyer, The Role of Oximes in the Management of Organophosphorus Pesticide Poisoning, Toxicol Rev. 2003: 22 (3): 165-190.
The National Institute for Occupational Safety and Health (NIOSH), Appendix B—Thirteen OSHA—Regulated Carcinogens, 2016, 1 page. https://www.cdc.gov/niosh/npg/nengapdxb.html.
Benjamin L. Van Duuren—Review—Comparison of Potency of Human Carcinogens: Vinyl Chloride, Chloromethylmethyl Ether and Bis(chloromethyl)ether, Environmental Research 49, 1989, 143-151.
Sylvia Wagner et al., Nanoparticulate Transport of Oximes over an In Vitro Blood-Brain Barrier Model, PLoS ONE, Dec. 2010, vol. 5, Issue 12, 10 pages.
Christina M. Wilhelm et al., A comprehensive evaluation of the efficacy of leading oxime therapies in guinea pigs exposed to organophosphorus chemical warfare agents or pesticides, Toxicology and Applied Pharmacology, 281, 2014, 12 pages.
Invitation to Pay Additional Fees and, Where Applicable, Protest Fee dated Jan. 11, 2021, issued in PCT International Patent Application No. PCT/US2020/070761, 2 pages.
International Search Report and Written Opinion dated Mar. 18, 2021, issued in PCT International Patent Application No. PCT/US2020/070761, 12 pages.
Amin et al., "Synthesis of Carbon-14 Labeled 1-(2-Hydroxyiminomethyl)-1 pyridino-3-(4-carbamoyl-1pyridino)-2-oxapropane Dichloride Monohydrate ([14C]H1-6-H2o)", Journal of Labelled Compounds and Radiopharmaceuticals, vol. XXXIX, No. 11, pp. 875-884, North Carolina, 1997.
Eyer et al., "HLö 7 dimethanesulfonate, a potent bispryridinium-dioxime against anticholinesterases", Archives of Toxicology, vol. 66, pp. 603-621, Germany, 1992.
Malinak et al., "A Review of the Synthesis of Quaternary Acetylcholinesterase Reactivators", Current Organic Chemistry, vol. 22, pp. 1619-1648, Czech Republic, 2018.

(Continued)

Primary Examiner — David K O'Dell

(74) Attorney, Agent, or Firm — Grossman, Tucker, Perreault & Pfleger, PLLC

(57) ABSTRACT

The present invention is directed at the synthesis and characterization of recrystallized HI-6 dimethylsulfate (DMS). The method can comprise dissolving HI-6 DMS in an alkyl-based glycol and adding an antisolvent to recrystallize HI-6 DMS or dissolving HI-6 DMS in methanol and adding dimethoxy ethane or dimethyl formamide as the antisolvent to recrystallize HI-6 DMS. The recrystallized HI-6 DMS indicates a resistance to moisture absorption and/or a DSC melting point onset (MP Onset) at least at or above 160.0° C.

5 Claims, 59 Drawing Sheets

(56) References Cited

OTHER PUBLICATIONS

Thiermann et al., "HI 6 dimethanesulfonate has better dissolution properties than HI 6 dichloride for application in dry/wet autoinjectors", International Journal of Pharmaceutics, vol. 137, pp. 167-176, Germany, 1996.
Extended European Search Report from related EPO Appln. No. 20887378.6, dated Oct. 20, 2023.

* cited by examiner

RECRYSTALLIZED HI-6 DIMETHYLSULFATE

FIELD

The present invention is directed at the synthesis and characterization of recrystallized HI-6 dimethylsulfate.

BACKGROUND

Organophosphorus nerve agents (OPNA), used as chemical weapons and pesticides, irreversibly inhibit AChE and cause an estimated 300,000 deaths per year worldwide. Currently, the bis-pyridinium oximes HLo-7 dimethylsulfate (DMS), HI-6 DMS and obidoxime DMS, are among the most effective reactivators of OPNA inhibited acetylcholinesterase (AChE). These antidotes have been reported to be in relatively short supply due to the use of bis(2-chloromethyl) ether (BCME) or bis(2-methylsulfonoxymethyl) ether (BMME), which are extremely carcinogenic, with an exposure limit of 0.0003 ppm.

There are additional challenges that need to be overcome in order to develop an injectable formulation for the warfighter. The antidote must be able to withstand the harsh conditions in which the warfighter is deployed, which is often cited as 40° C. for up to two years and once poisoned, the antidote needs to work rapidly. Complicating matters is the fact that the bis-pyridinium oxime antidotes are not stable in water for long periods of time, making simple aqueous formulations not feasible. Wet-dry or emulsion injectable formulations must be used and thus the qualities of the solid antidote must be considered when developing these formulations. The solids are ideally minimally hydroscopic, relatively stable at high temperatures for long periods of time, not clog the needle of an auto-injector and dissolve relatively quickly in either the body or water if a wet-dry injector is used.

SUMMARY

The present invention relates to a method for producing a HI-6 DMS in recrystallized form comprising dissolving HI-6 DMS in an alkyl-based glycol and adding an antisolvent to precipitate recrystallized HI-6 DMS The alkyl-based glycol may preferably comprise ethylene glycol or 1,2-propane diol.

The present invention also relates to a method for producing a HI-6 DMS in recrystallized form comprising dissolving HI-6 DMS in methanol and adding dimethoxy ethane or dimethyl formamide to precipitate recrystallized HI-6 DMS.

The present invention also relates to a method for producing a HI-6 DMS in recrystallized form comprising dissolving HI-6 DMS in ethylene glycol and adding tert-butanol to precipitate recrystallized HI-6 DMS wherein said recrystallized form does not absorb water over a seven-day period under ambient temperature and humidity conditions.

The present invention also relates to a method for producing a HI-6 DMS in recrystallized form comprising dissolving HI-6 DMS in 1,2-propane diol and adding tert-butanol to precipitate HI-6 DMS in recrystallized form wherein said recrystallized form does not absorb water over a seven-day period under ambient temperature and humidity conditions.

FIGURES

FIG. 1A provides an image of unprocessed HI-6 at the magnification of 10×.

FIG. 1B provides an image of unprocessed HI-6 at the magnification of 20×.

FIGS. 2A, 2B and 2C provide images of HI-6 DMS recrystallized from the single solvent system of methanol at the magnification of 5×, 10× and 20×, respectively.

FIGS. 3A, 3B and 3C provides images of recrystallized HI-6 DMS recovered from the binary solvent system MeOH:tBuOH (1:3) at the indicated magnifications of 5×, 10× and 20×, respectively.

FIGS. 4A, 4B and 4C provides images of recrystallized HI-6 DMS recovered from the binary solvent system MeOH:DME (1:1) at the indicated magnifications of 5×, 10× and 20×, respectively.

FIGS. 5A, 5B and 5C provides images of recrystallized HI-6 DMS recovered from the binary solvent system MeOH:DMF (1:2) at the indicated magnifications of 5×, 10× and 20×, respectively.

FIGS. 6A, 6B and 6C provides images of recrystallized HI-6 DMS recovered from the binary solvent system MeOH:EtOH (1:1) at the indicated magnifications of 5×, 10× and 20×, respectively.

FIGS. 7A, 7B and 7C provide images of recrystallized HI-6 DMS from the binary solvent system MeOH:MeCN (1:15) at the indicated magnifications of 5×, 10× and 20×, respectively.

FIGS. 8A, 8B and 8C provide images of recrystallized HI-6 DMS from the single solvent system of ethylene glycol at the indicated magnifications of 5×, 10× and 20×, respectively. A relatively small amount of t-BuOH was utilized to promote crystallization.

FIGS. 9A, 9B and 9C provide images of recrystallized HI-6 DMS from the binary solvent system of ethylene glycol/EtOH (1:8) at the indicated magnifications of 5×, 10× and 20×, respectively.

FIGS. 10A, 10B and 10C provide image of recrystallized HI-6 DMS from the binary solvent system of ethylene glycol/MeCN (1:1) at the indicated magnifications of 5×, 10× and 20×, respectively.

FIGS. 11A, 11B and 11C provides images of recrystallized HI-6 DMS from the binary solvent system of ethylene glycol/t-BuOH (1:4) at the indicated magnifications of 5×, 10× and 20×, respectively.

FIGS. 12A, 12B and 12C provide images of recrystallized HI-6 DMS from the single solvent system of propylene glycol (1,2-propane diol) at the indicated magnifications of 5×, 10× and 20×, respectively. A relatively small amount of t-BuOH was utilized to promote crystallization.

FIGS. 13A, 13B and 13C provide images of recrystallized HI-6 DMS from the binary solvent system of propylene glycol/DME (1:9) at the indicated magnifications of 5×, 10× and 20×, respectively.

FIGS. 14A, 14B and 14C provide images of recrystallized HI-6 DMS from the binary solvent system of propylene glycol/EtOH (1:5) at the indicated magnifications of 5×, 10× and 20×, respectively.

FIGS. 15A, 15B and 15C provide images of recrystallized HI-6 DMS from the binary solvent system of propylene glycol/MeCN (1:5) at the indicated magnifications of 5×, 10× and 20×, respectively.

FIGS. 16A, 16B and 16C provide images of recrystallized HI-6 DMS from the binary solvent system of propylene glycol/tBuOH (1:2) at the indicated magnifications of 5×, 10× and 20×, respectively.

FIGS. 17A, 17B and 17C provide images of recrystallized HI-6 DMS from the single solvent system of water at the indicated magnifications of 5×, 10× and 20×, respectively.

FIGS. 18A, 18B and 18C provide images of recrystallized HI-6 DMS from the binary solvent system of water/EtOH (1:14) at the indicated magnifications of 5×, 10× and 20×, respectively.

FIGS. 19A, 19B and 19C provide images of recrystallized HI-6 DMS from the binary solvent system of water/DMF (1:23) at the indicated magnifications of 5×, 10× and 20×, respectively.

DETAILED DESCRIPTION

Figure 1A:
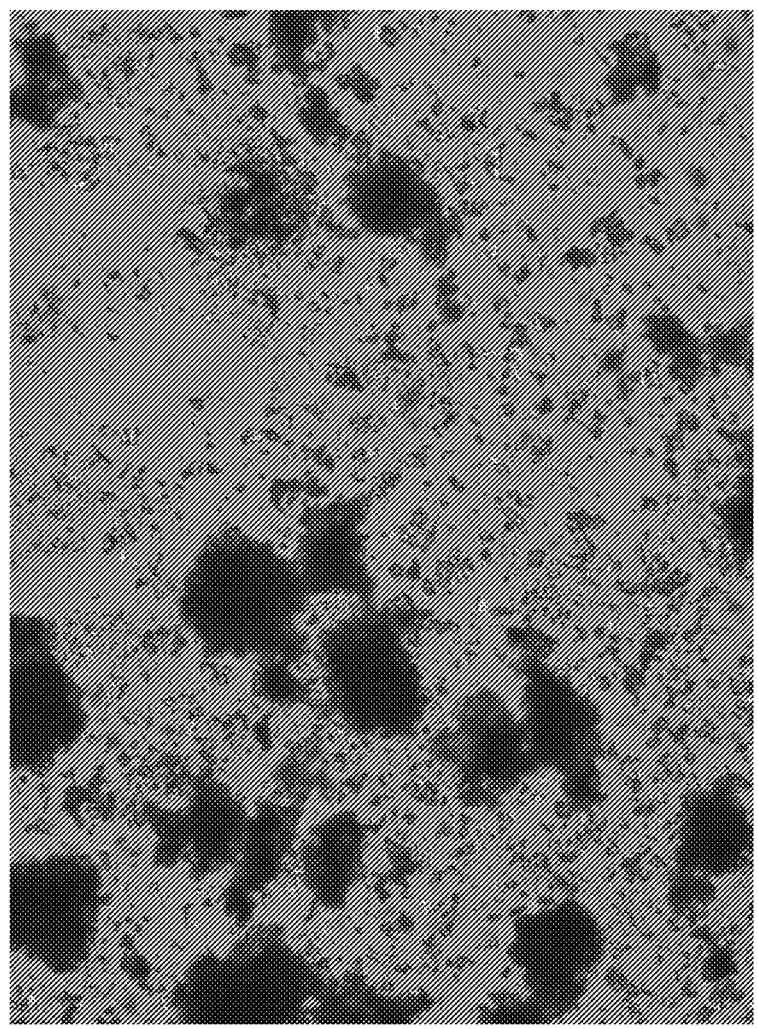

The present invention relates to the synthesis and characterization of recrystallized HI-6 dimethylsulfate (DMS). HI-6 DMS is otherwise identified as (1-(2-(hydroxyiminomethyl)pyridinium)-3-(4-carbamoylpyridinium)-2-oxapropane) DMS, whose structure is illustrated below:

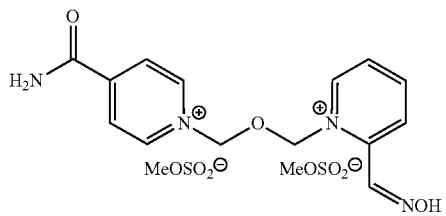

It was determined herein that preferably, to prepare a recrystallized form of HI-6 DMS, one can now utilize a polyol solvent, which is reference herein to an alkyl-based glycol, which is reference to an aliphatic carbon-hydrogen structure containing at least two hydroxy groups. Preferably ethylene glycol and/or 1,2-propane diol. Table 1 below identifies the maximum solubility of HI-6 DMS in the indicated solvents:

TABLE 1

HI-6 DMS Solvents

| Solvent | Maximum Solubility (% w/w) |
| --- | --- |
| Water | 118.35 |
| Ethylene Glycol | 14.153 |
| Methanol | 7.577 |
| 1,2-Propane Diol | 2.847 |

In connection with Table 1 above, it was observed that HI-6 DMS was highly soluble in the alkylene glycol glycerol, but that there was no saturation point (i.e. maximum solubility) observed as the solution became too viscous.

Next, a series of antisolvents were identified, where the maximum solubility of HI-6 DMS in such antisolvents is shown below in Table 2. Reference to an antisolvent is a solvent that can be combined with the HI-6 DMS when dissolved in the preferred solvents in Table 1 (i.e. ethylene glycol and/or 1,2-propane diol) to provoke precipitation and recrystallization of the HI-6 DMS.

TABLE 2

HI-6 DMS Antisolvents

| AntiSolvent | Maximum Solubility (% w/w) |
| --- | --- |
| Dimethyoxy ethane | 0.338 |
| Tert-butanol | 0.257 |
| Acetonitrile | 0.124 |
| DMF | 0.1067 |
| Ethanol | 0.056 |
| Isopropyl alcohol | 0.03 |

It is noted that single solvent recrystallization was conducted for comparison to the binary solvent systems noted above (i.e. solvent/antisolvent). For the comparative single solvent recrystallization, methanol and water were utilized as the solvent followed by cooling to provide for precipitation and recrystallization. Methanol and water were observed to produce crystals upon cooling to room temperature. In addition, when the diols were employed as a single solvent system (ethylene diol and 1,2-propane diol), they would produce oils when concentrating such solutions. However, when such oils were then treated with a relatively small amount (e.g., up to ~1.0 ml) of an antisolvent, such as tert-butanol, the oils would otherwise crystallize.

In Table 3 below, a summary is provided regarding the use of identified binary solvent system with the identified solvent "A" and the identified non-solvent "B":

TABLE 3

Binary Solvent System For HI-6 Recrystallization

| | Antisolvent B | | | | | | | | | |
| --- | --- | --- | --- | --- | --- | --- | --- | --- | --- | --- |
| | t-BuOH | | MeCN | | EtOH | | DMF | | DME | |
| | Ratio (A:B) | mL | Ratio (A:B) | mL | Ratio (A:B) | mL | Ratio (A:B) | mL | Ratio (A:B) | mL |
| Solvent A | | | | | | | | | | |
| MeOH | 1:3 | 4 | 1:15 | 16 | 1:1 | 2 | 1:2 | 2 | 1:1 | 2 |
| ethylene glycol | 1:4 | 5 | 1:11 | 11 | 1:8 | 9 | N/A | | N/A | |
| 1,2-propane diol | 1:2 | 3 | 1:5 | 6 | 1:5 | 5 | N/A | | 1:9 | 10 |
| Water | N/A | | N/A | | 1:14 | | 1:23 | | N/A | |

As can be seen from the above, using methanol (MeOH), ethylene glycol, 1,2-propane diol and water as the solvent, and tert-butanol (t-BuOH), acetonitrile (MeCN), ethanol (EtOH), dimethylformamide (DMF) and dimethoxy ethane (DME), one was able to identify which binary combinations produced crystals and at what ratios. In the Table 3, reference to N/A are those binary solvent systems that were observed to produce oils instead of observed crystal formation. When crystals were formed they could be readily isolated by filtration. Accordingly, it can be seen that ethylene glycol and 1,2-propane diol can be utilized as solvent for HI-6 DMS wherein the addition of an antisolvent (e.g., t-BuOH, MeCN or EtOH) results in recrystallization.

Samples of the HI-6 DMS crystal polymorphs produced from the binary solvent systems (Table 3) as well as the comparative samples (produced from a single solvent system noted herein) were dried under vacuum for 12-16 hours and then analyzed by differential scanning calorimetry (DSC) at a heating rate of 10° C. per minute. Melting point onset was defined by the inflection point of the DSC endotherm from the DSC baseline and the melting point was then defined as the peak in the observed endothermic tracing provided by the DSC. The decomposition temperature herein is reference to the decomposition onset which is defined as that temperature where the DSC tracing deviated from the DSC baseline followed by a relatively erratic trace. The results are summarized below in Tables 4 and 5:

TABLE 4

Recrystallized HI-6 Characterization By DSC

| Solvent | Antisolvent | Mp Onset (° C.) | Mp (° C.) | Decomp. (° C.) |
|---|---|---|---|---|
| Ethylene Glycol | N/A | 160.48 | 165.87 | 168.11 |
| | t-BuOH | 133.42 | 140.5 | 146.96 |
| | MeCN | N/A | N/A | 164.41 |
| | EtOH | 134.86 | 144.34 | 153.27 |
| Methanol | N/A | 118.22 | 133.93 | 137.25 |
| | t-BuOH | 162.93 | 170.97 | 172.01 |
| | EtOH | 167.03 | 172.37 | 172.94 |
| | DME | N/A | N/A | 166.08 |
| | DMF | 165.26 | 168.08 | 169.79 |
| | MeCN | 161.26 | 167.07 | 168.2 |
| 1,2-propane diol | N/A | 144.87 | 149.07 | 161.51 |
| | EtOH | 140.9 | 147.22 | 150.71 |
| | MeCN | 146.23 | 153.7 | 157.45 |
| | DME | 163.39 | 167.08 | 167.99 |
| | t-BuOH | 142.68 | 144.4 | 149.15 |
| H₂O | N/A | 131.11 | 135.40 | 142.80 |
| | EtOH | NA | NA | 167.61 |
| | DMF | 161.98 | 170.19 | 171.62 |
| Unprocessed HI-6 | N/A | 162.33 | 168.08 | 168.87 |
| Average | N/A | 149.81 | 156.14 | 160.88 |

In the above table, reference to "N/A" in the "Mp Onset" or "Mp" column is reference to the observation that the sample would decompose prior to melting. In the case of ethylene glycol and 1,2-propane diol, reference to "N/A" in the column "Antisolvent" is reference to the fact that, as noted above, when such solvents were employed on their own and concentrated, such would lead to oil formation which oil could then be converted to recrystallized HI-6 DMS upon treatment with a relative small amount (e.g. up to ~1.0 ml) of tert-butanol.

TABLE 5

Summary Of DSC Analysis In Table 4

| | Averages | | | | | |
|---|---|---|---|---|---|---|
| Solvent | Mp Onset (° C.) | Δ Ave | Mp (° C.) | Δ Ave | Decomp. (° C.) | Δ Ave |
| t-BuOH | 146.34 | −3.47 | 151.96 | −4.18 | 156.04 | −4.84 |
| EtOH | 147.6 | −2.21 | 154.64 | −1.5 | 161.13 | 0.25 |
| DME | 163.39 | 13.58 | 167.08 | 10.94 | 167.04 | 6.16 |
| DMF | 163.62 | 13.81 | 169.14 | 13 | 170.71 | 9.83 |
| MeCN | 153.75 | 3.94 | 160.39 | 4.25 | 163.35 | 2.47 |
| Ethylene Glycol | 142.92 | −6.89 | 150.24 | −5.9 | 156.11 | −4.77 |
| MeOH | 154.94 | 5.13 | 162.48 | 6.34 | 164.04 | 3.16 |
| 1,2-propane diol | 147.61 | −2.2 | 152.29 | −3.85 | 157.36 | −3.52 |
| H₂O | 146.55 | −3.26 | 152.8 | −3.34 | 157.21 | −3.67 |
| Average | 149.81 | N/A | 156.14 | N/A | 160.88 | N/A |

As can be seen, Table 4 identifies the particular solvent and non-solvent combination that were evaluated. Table 5 provides the average values of melting point onset, melting point, and decomposition temperature from Table 4 when generally using the identified antisolvent B (t-BuOH, EtOH, DME, DMF and MeCN). In addition, Table 4 then provides such average values when specifically using ethylene glycol, MeOH, 1,2-propane diol and water, in the particular binary solvent systems identified in Table 4. As can be seen, HI-6 DMS can be: (1) dissolved in ethylene glycol and caused to precipitate and recrystallize upon addition of antisolvents t-BuOH and EtOH; (2) dissolved in 1,2-propane diol and caused to precipitate and recrystallize upon addition of antisolvents EtOH, MeCN, DME and t-BuOH. As can also be observed from Table 5, when using DME or DMF as antisolvents, values for Mp Onset, Mp and Decomposition Temperature determined by DSC were relatively higher than for other antisolvents. As can be seen, the MP Onset was at least at or above 160.0° C. and Mp was at least at or above 165.0° C.

Figure 1B:
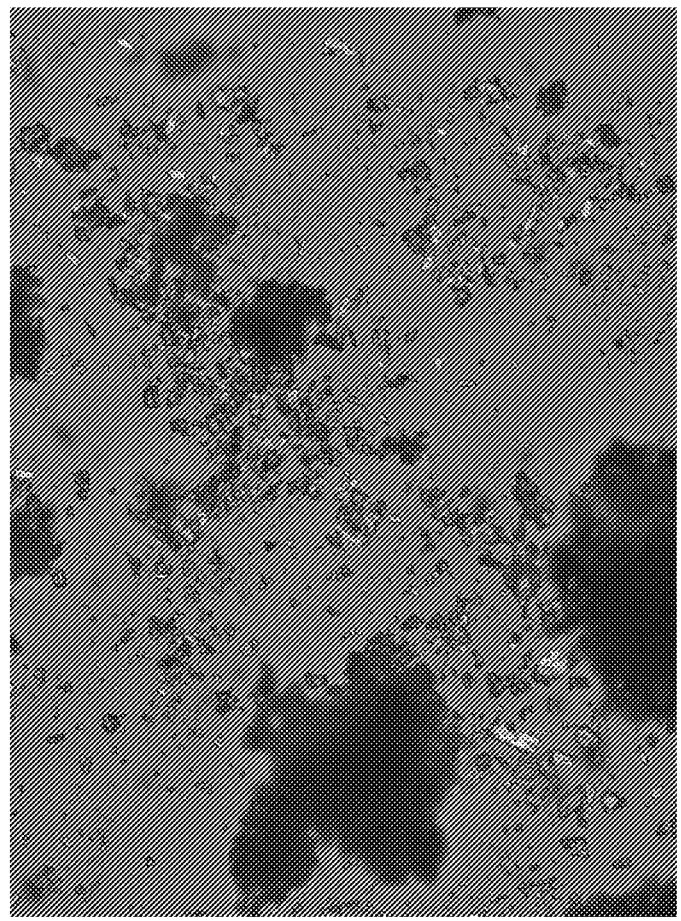

FIG. 1A and FIG. 1B herein provides images of unprocessed HI-6 at the indicated magnifications 10× and 20×, respectively.

Figure 2A:
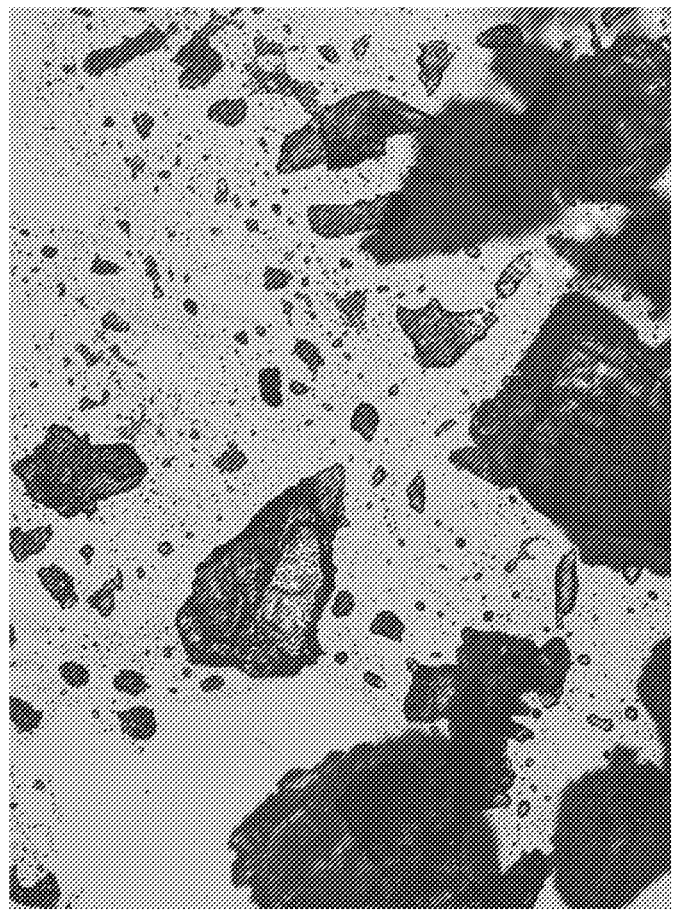
Figure 2B:
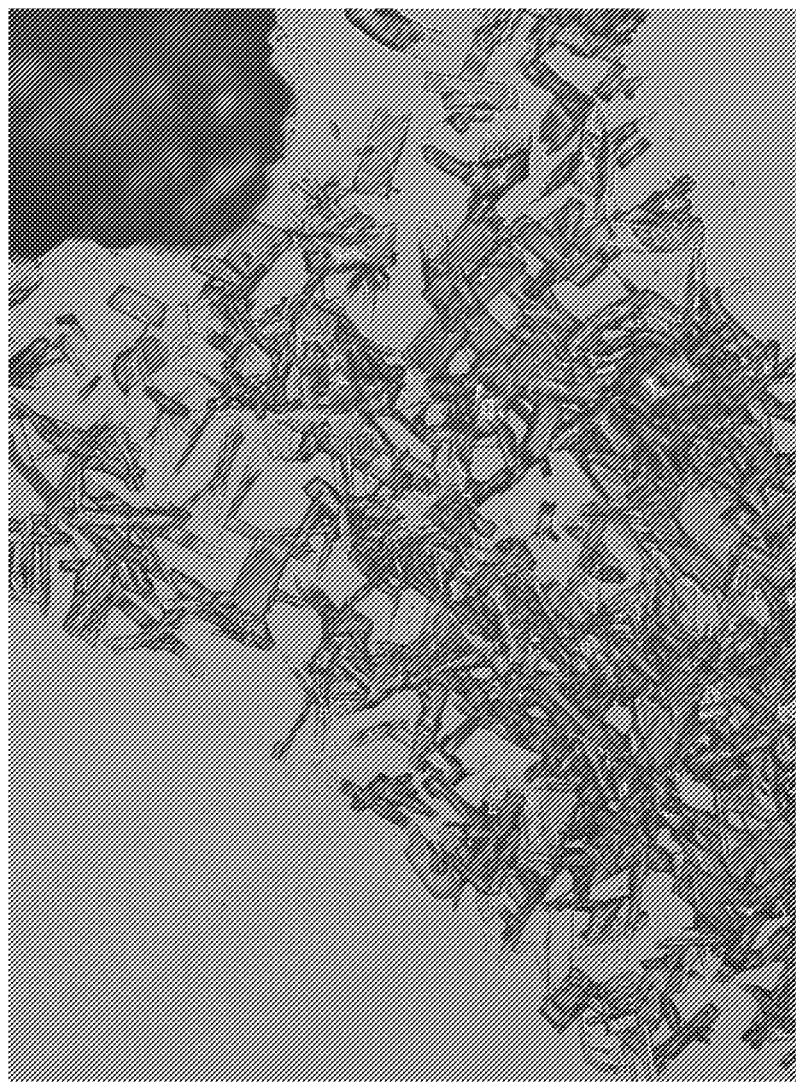
Figure 2C:

FIGS. 2A, 2B and 2C provide images of recrystallized HI-6 DMS recovered from the single solvent system of methanol at the indicated magnifications of 5×, 10× and 20× respectively.

Figure 3A:
Figure 3B:
Figure 3C:
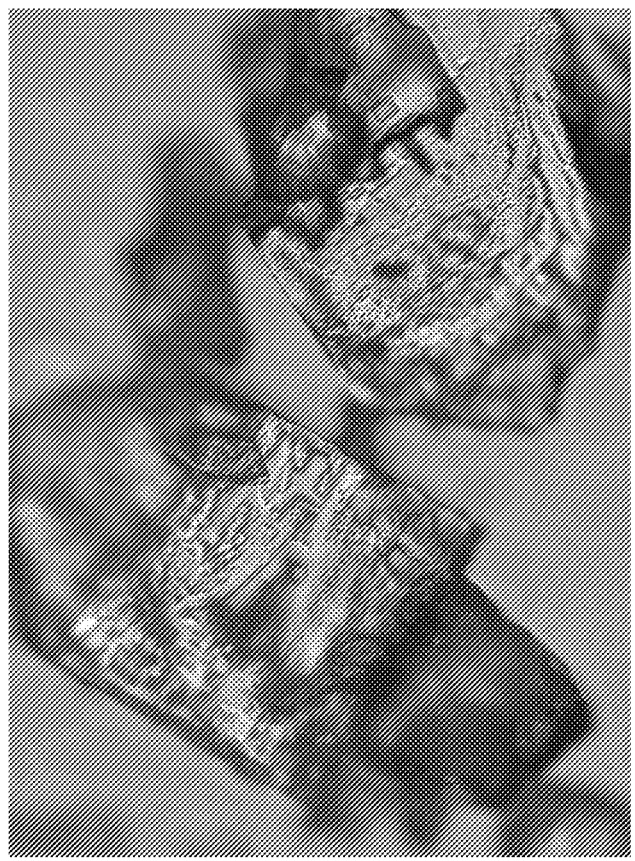

FIGS. 3A, 3B and 3C provides images of recrystallized HI-6 DMS recovered from the binary solvent system MeOH:tBuOH (1:3) at the indicated magnifications of 5×, 10× and 20×, respectively.

Figure 4A:
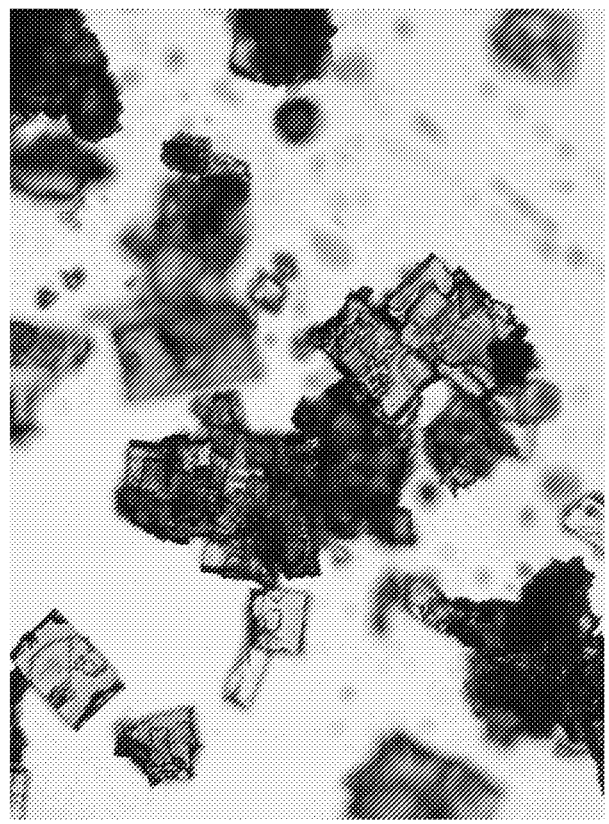
Figure 4B:
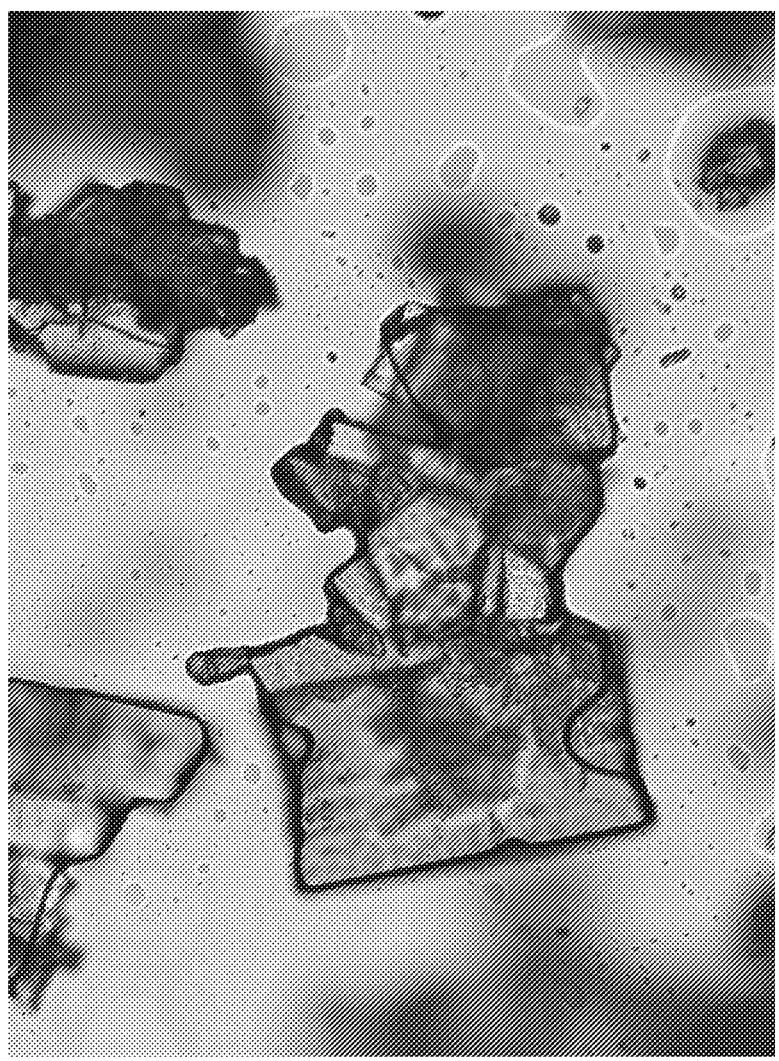
Figure 4C:
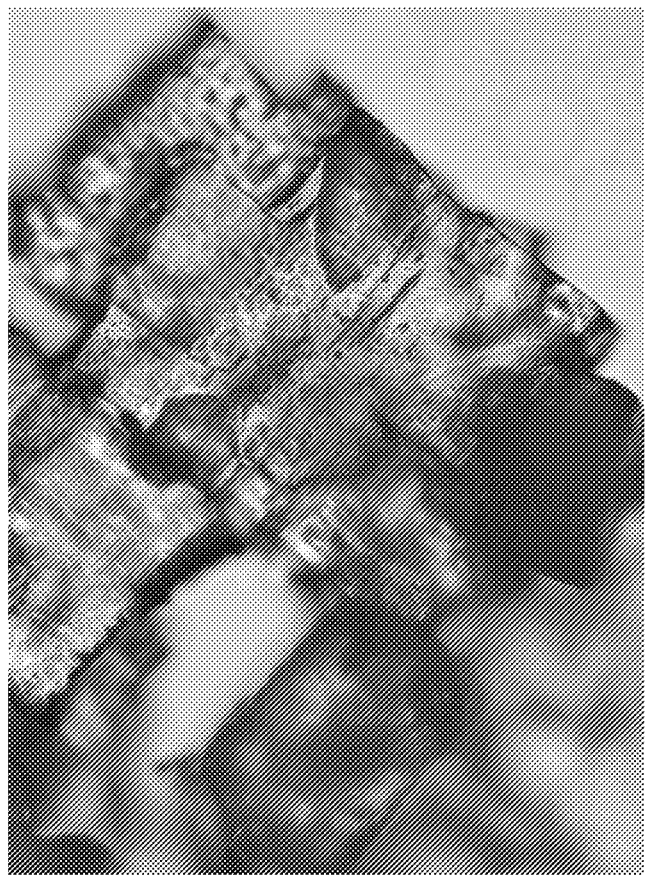

FIGS. 4A, 4B and 4C provides images of recrystallized HI-6 DMS recovered from the binary solvent system MeOH:DME (1:1) at the indicated magnifications of 5×, 10× and 20×, respectively.

Figure 5A:
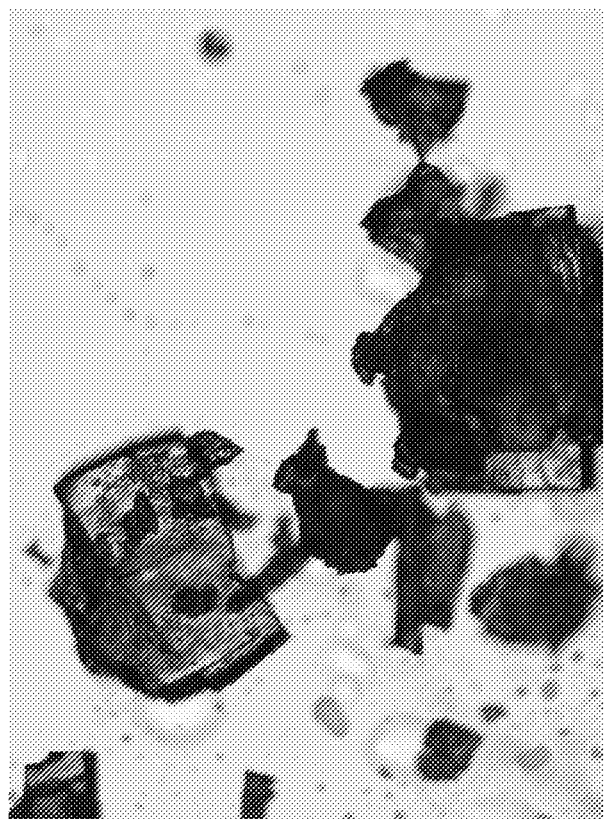
Figure 5B:
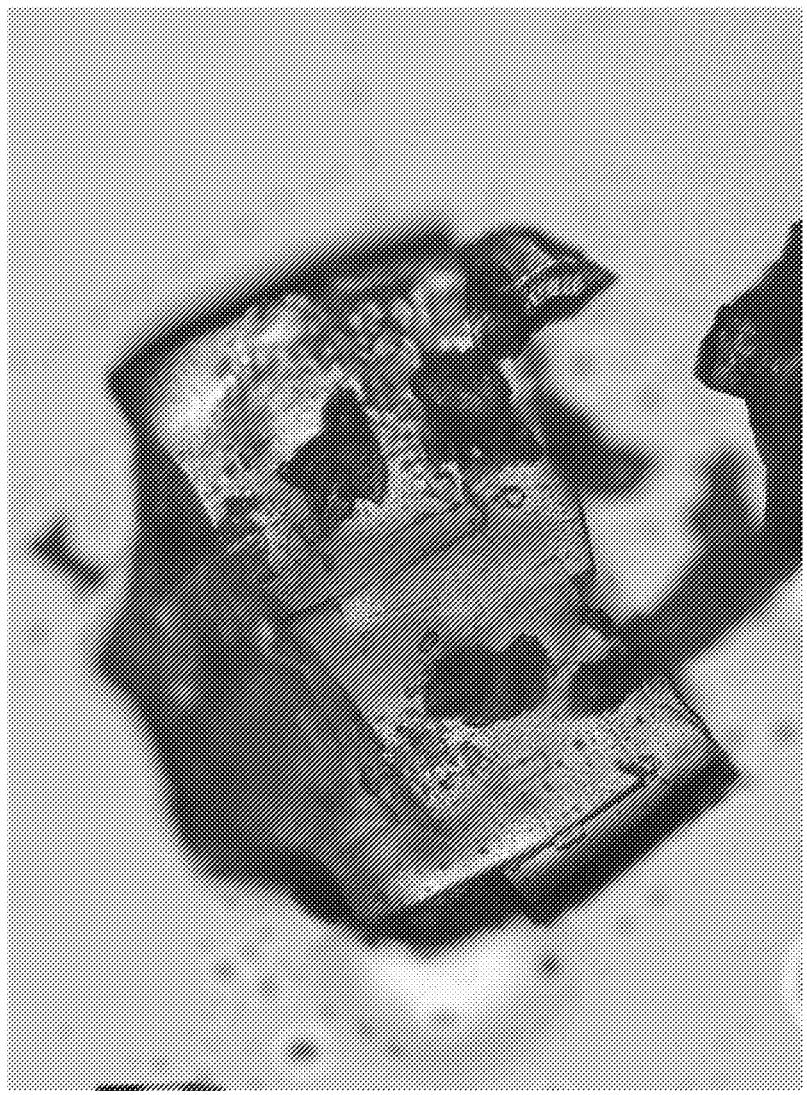
Figure 5C:
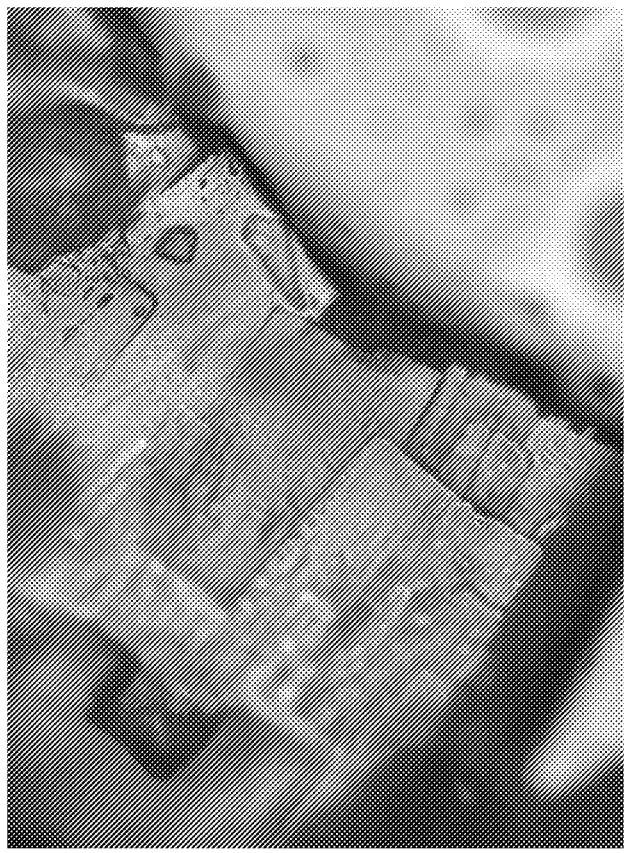

FIGS. 5A, 5B and 5C provides images of recrystallized HI-6 DMS recovered from the binary solvent system MeOH:DMF (1:2) at the indicated magnifications of 5×, 10× and 20×, respectively.

Figure 6A:
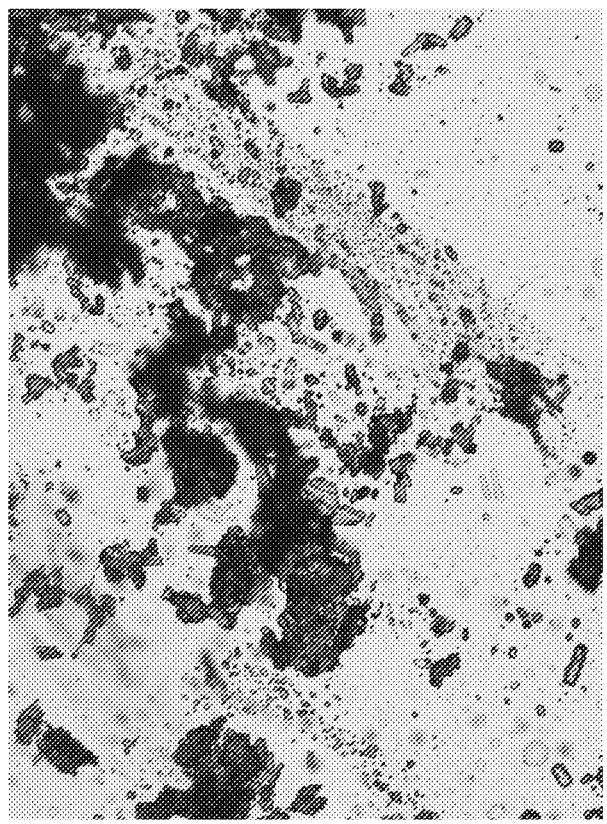
Figure 6B:
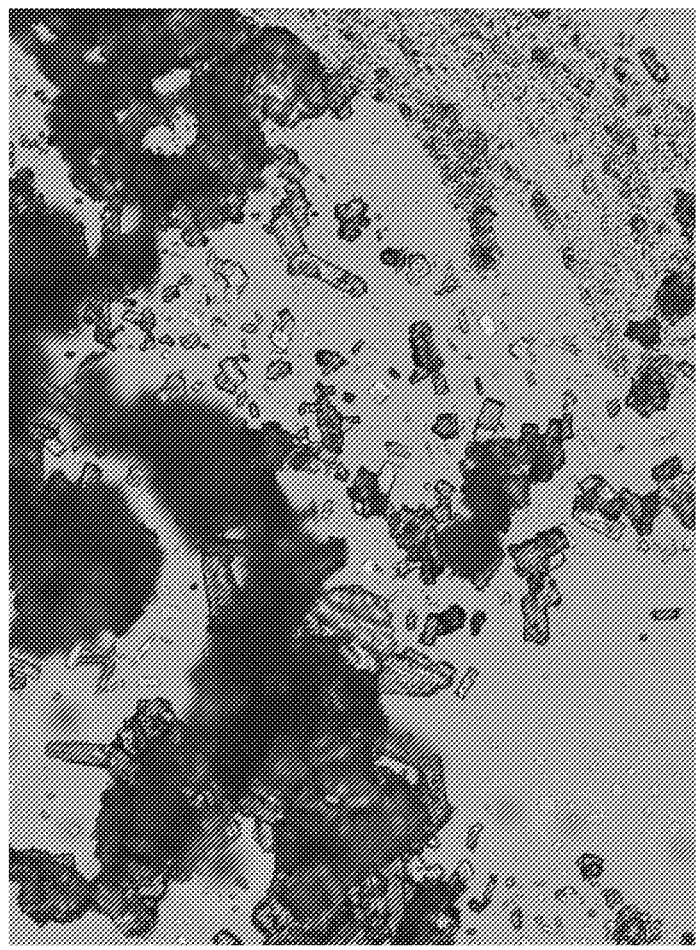
Figure 6C:
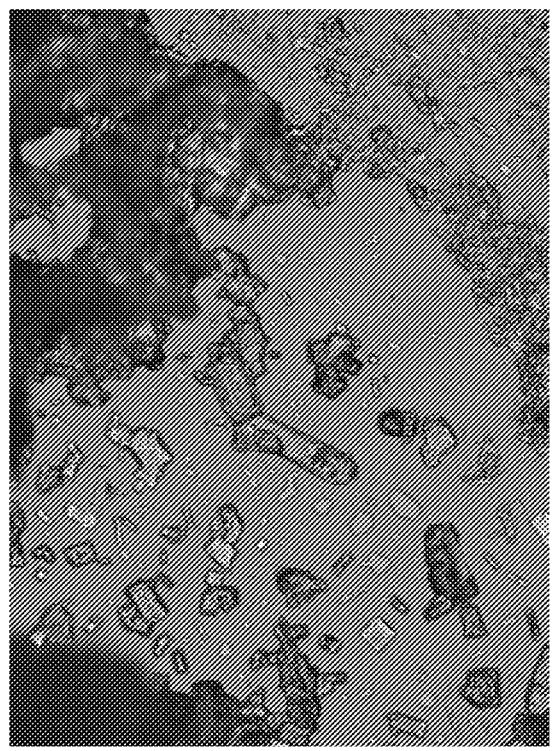

FIGS. 6A, 6B and 6C provides images of recrystallized HI-6 DMS recovered from the binary solvent system MeOH:EtOH (1:1) at the indicated magnifications of 5×, 10× and 20×, respectively.

Figure 7A:
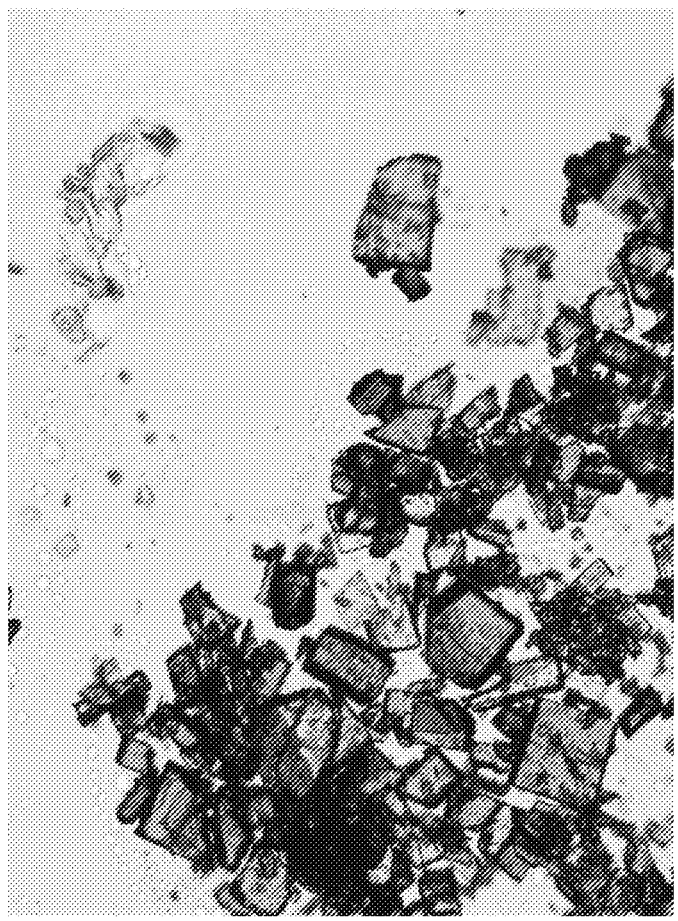
Figure 7B:
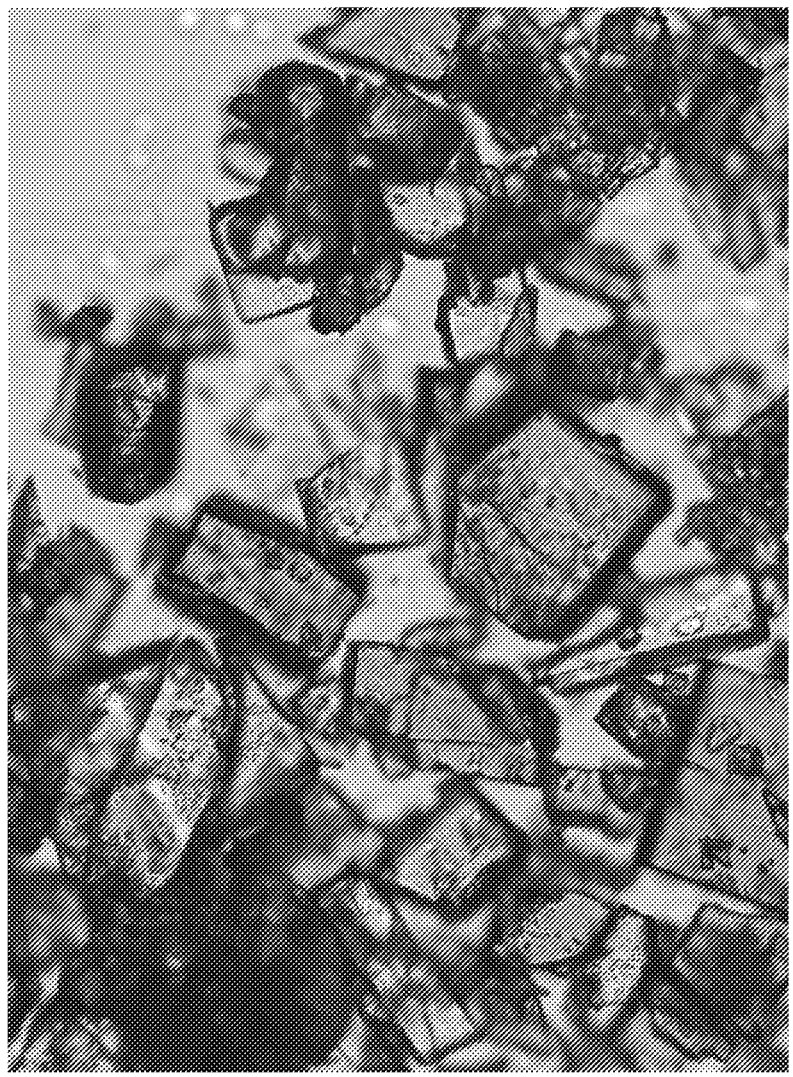
Figure 7C:
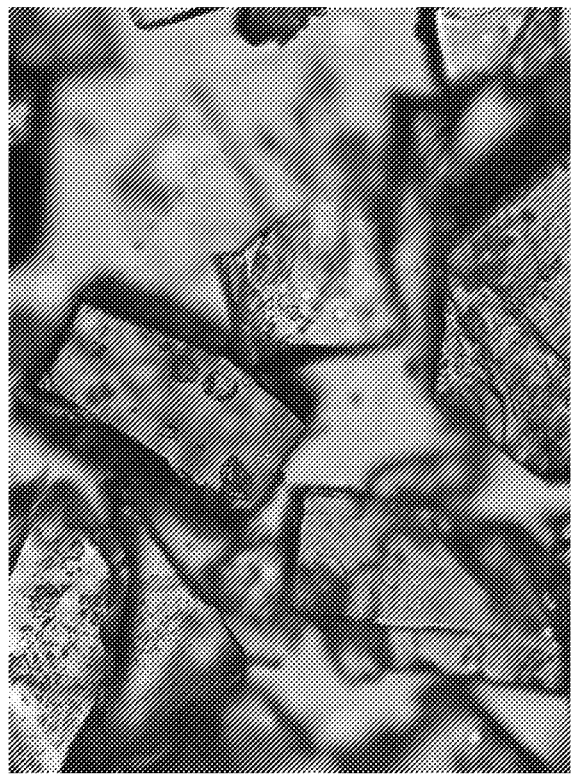

FIGS. 7A, 7B and 7C provide images of recrystallized HI-6 DMS from the binary solvent system MeOH:MeCN (1:15) at the indicated magnifications of 5×, 10× and 20×, respectively.

Figure 8A:
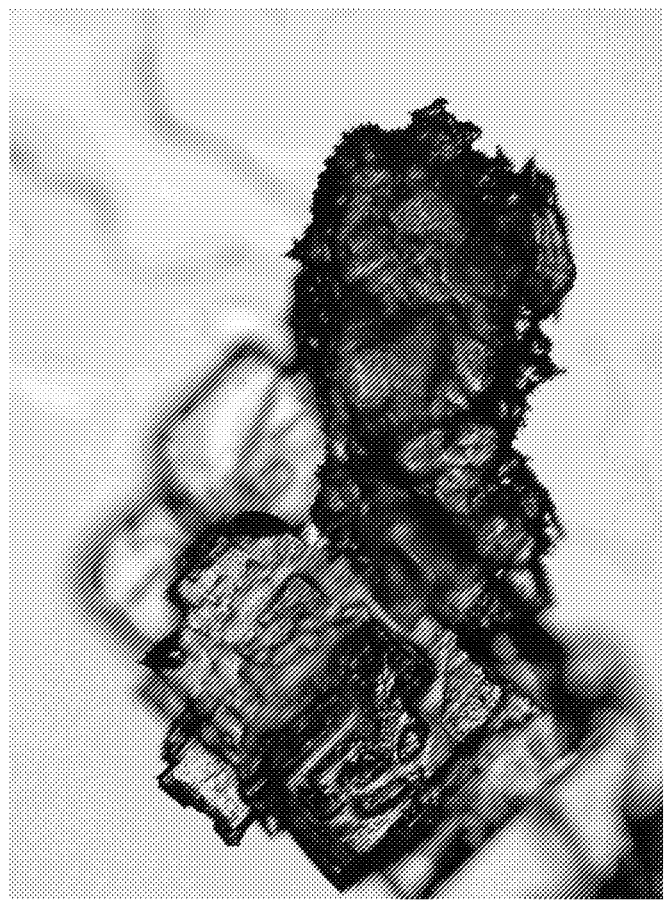
Figure 8B:
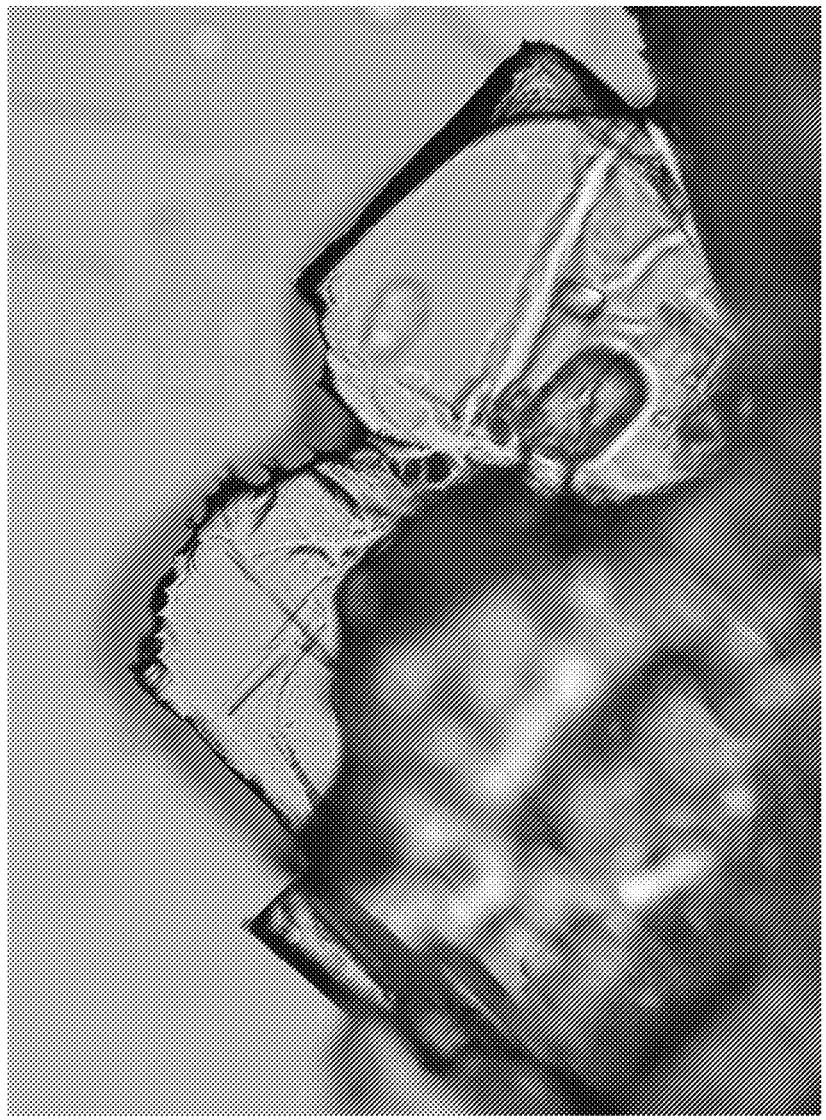
Figure 8C:
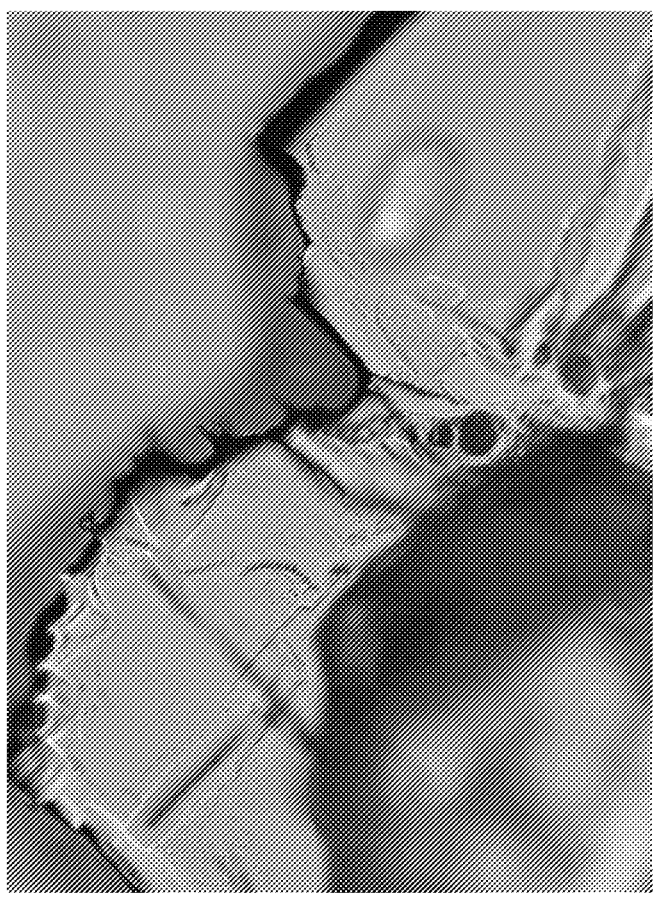

FIGS. 8A, 8B and 8C provide images of recrystallized HI-6 DMS from the single solvent system of ethylene glycol at the indicated magnifications of 5×, 10× and 20×, respectively. A relatively small amount of t-BuOH was utilized to promote crystallization.

Figure 9A:
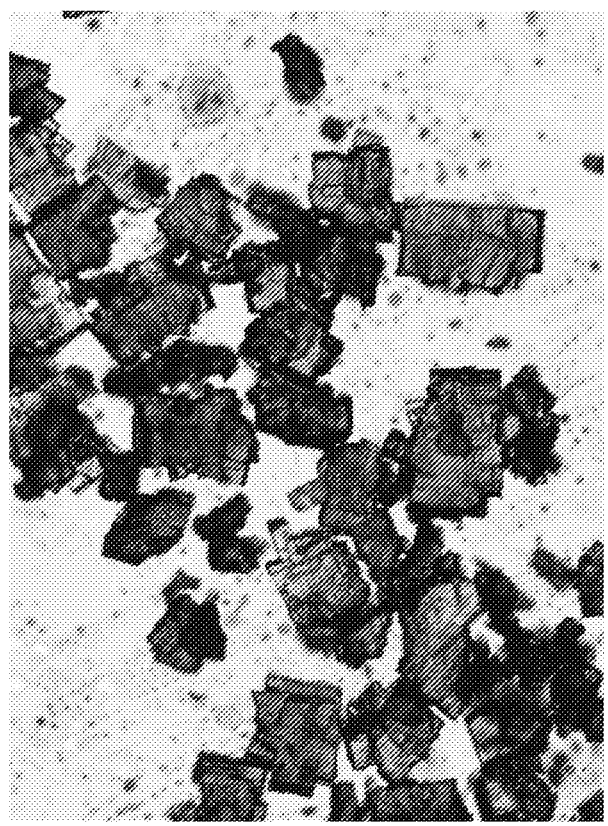
Figure 9B:
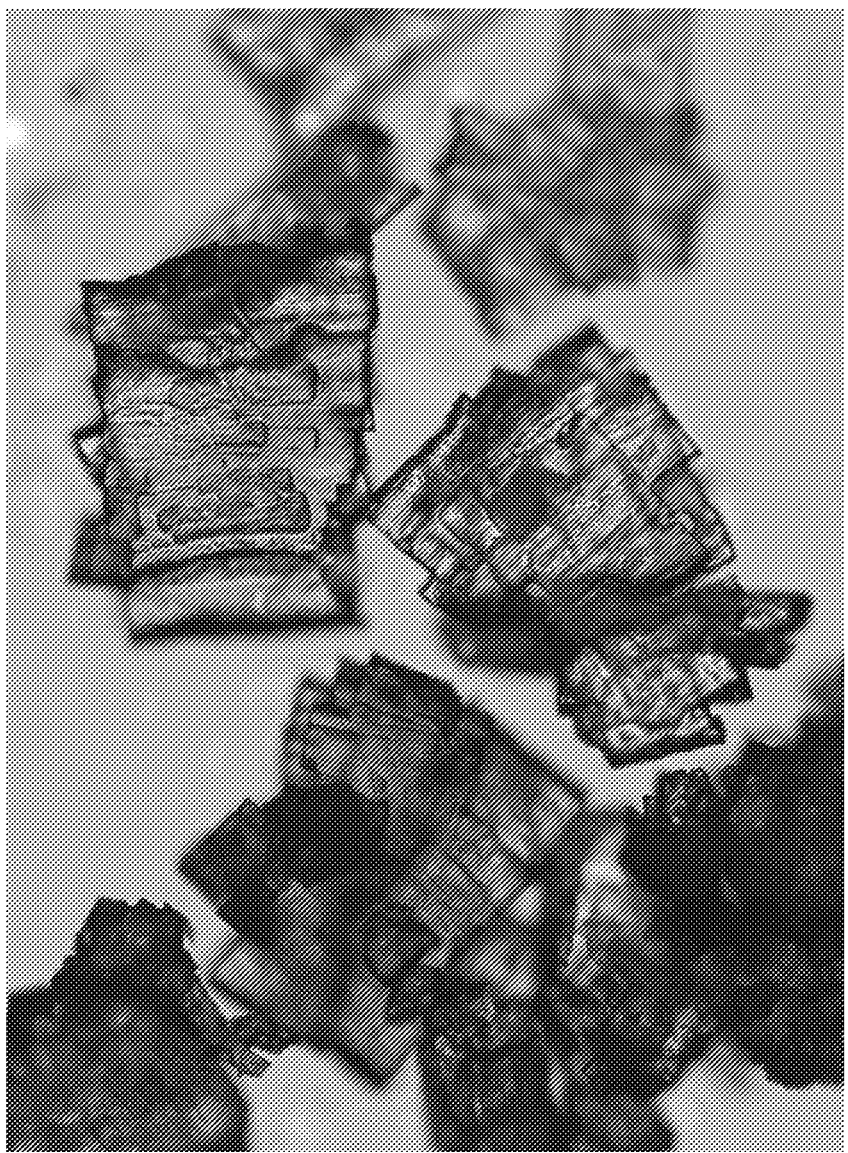
Figure 9C:
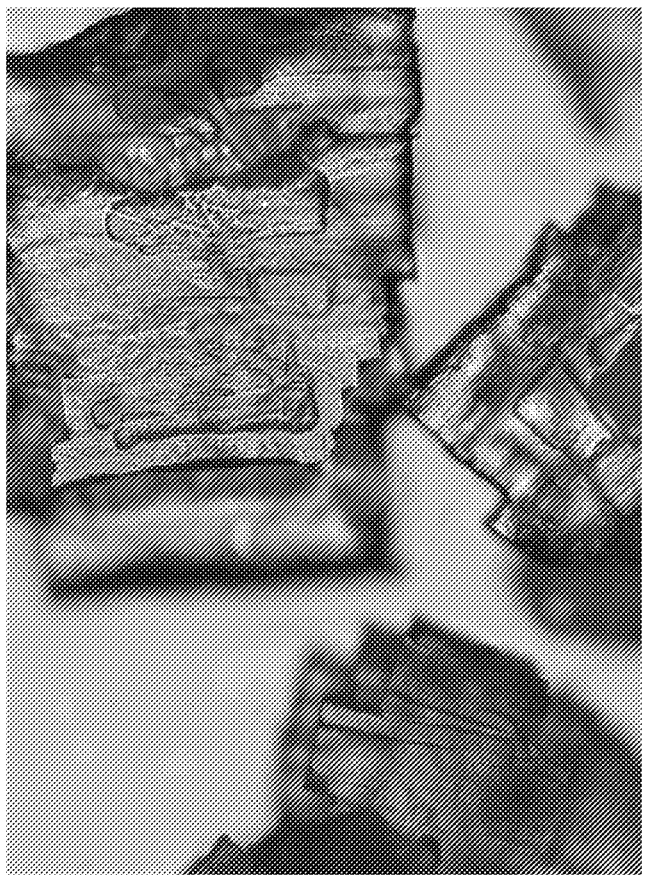

FIGS. 9A, 9B and 9C provides images of recrystallized HI-6 DMS from the binary solvent system of ethylene glycol/EtOH (1:8) at the indicated magnifications of 5×, 10× and 20×, respectively.

Figure 10A:
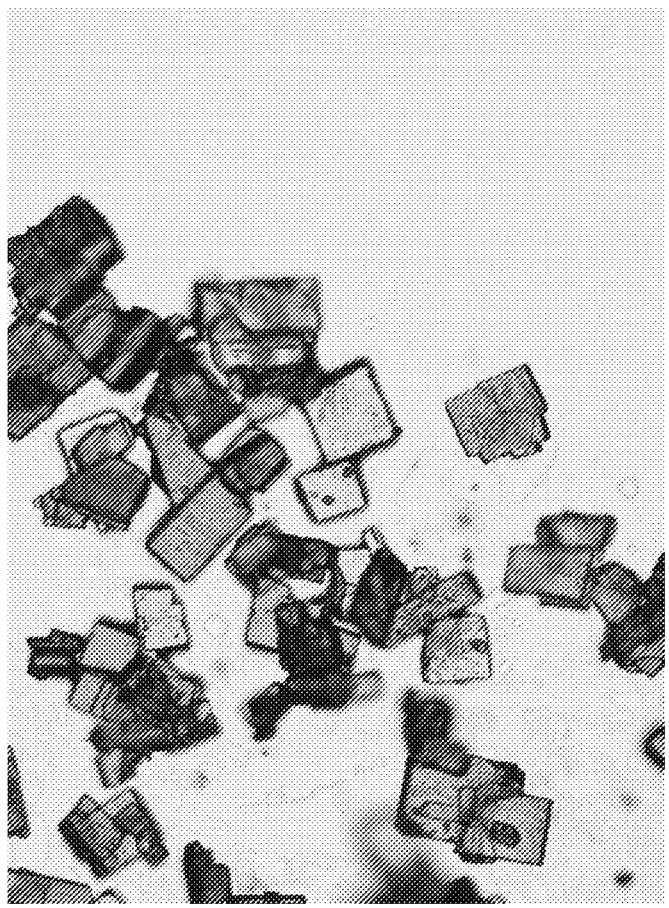
Figure 10B:
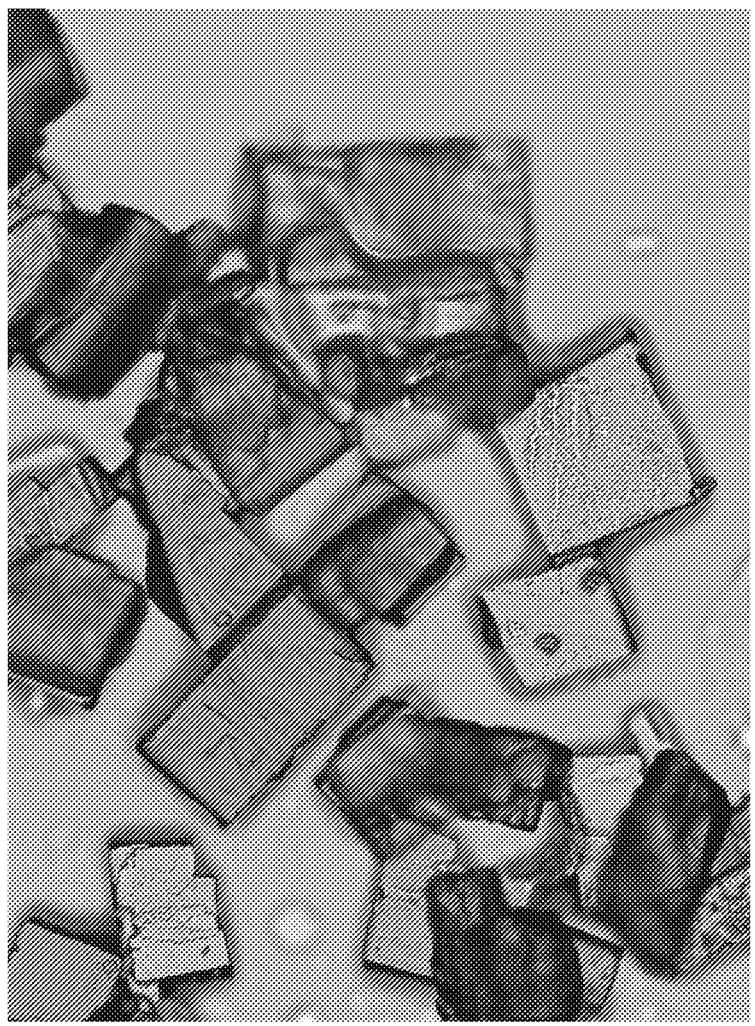
Figure 10C:
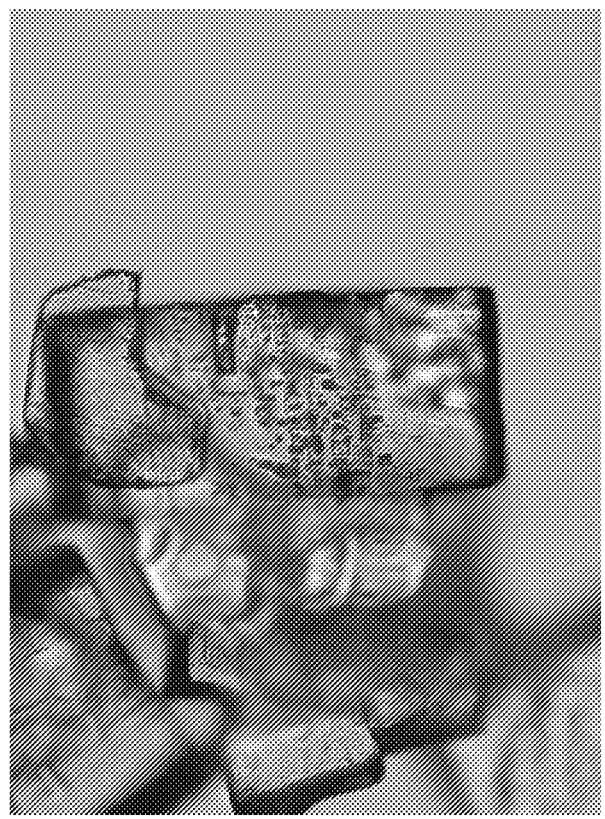

FIGS. 10A, 10B and 10C provide image of recrystallized HI-6 DMS from the binary solvent system of ethylene glycol/MeCN (1:1) at the indicated magnifications of 5×, 10× and 20×, respectively.

Figure 11A:
Figure 11B:
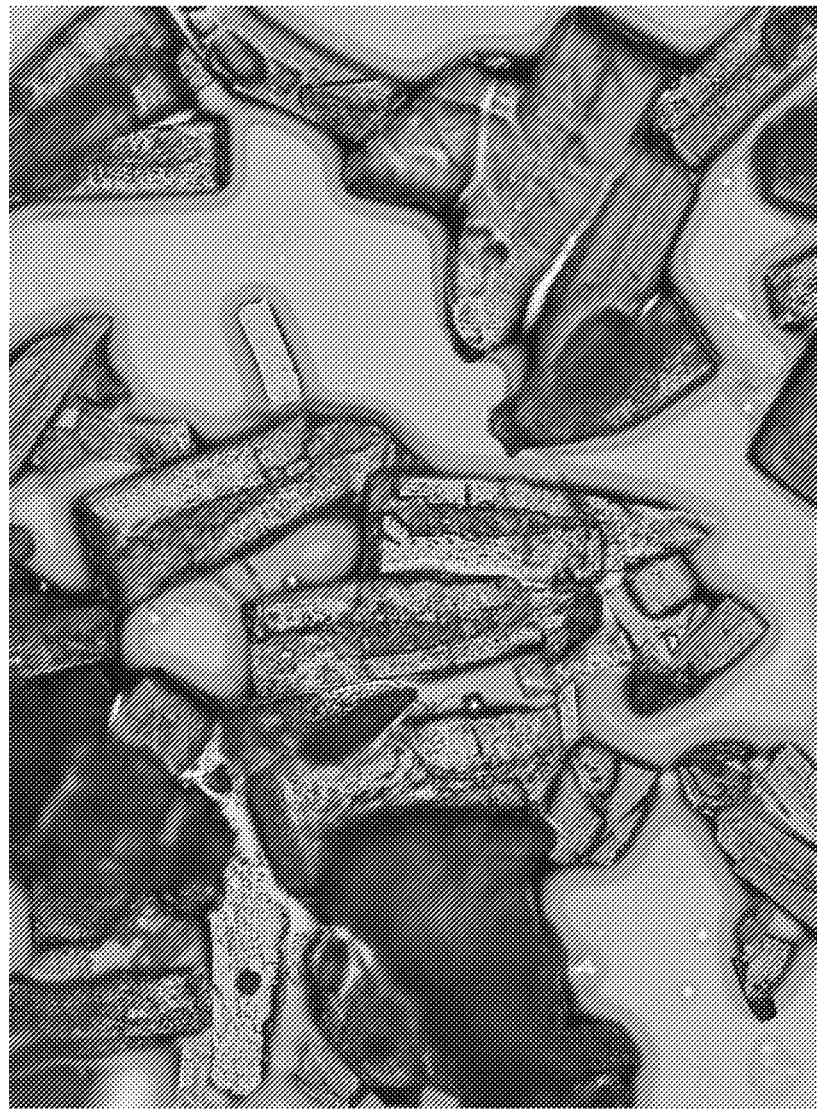
Figure 11C:
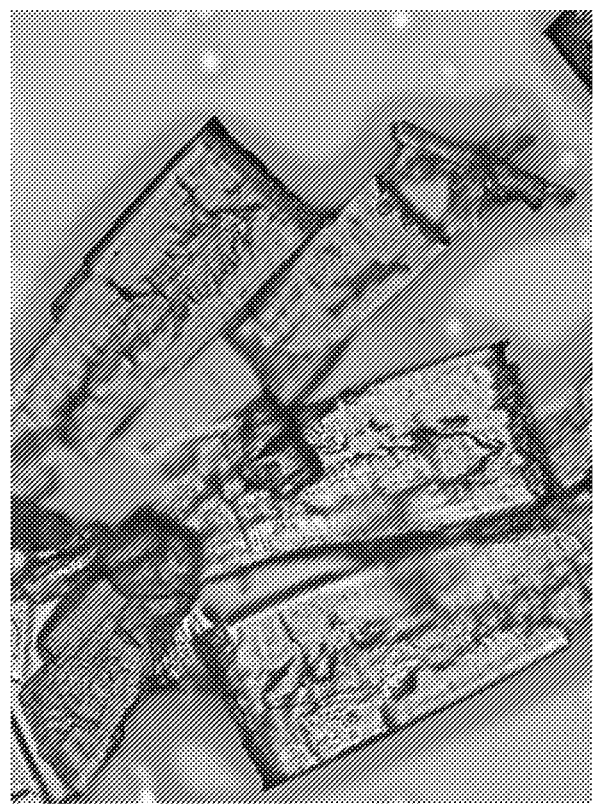

FIGS. 11A, 11B and 11C provides images of recrystallized HI-6 DMS from the binary solvent system of ethylene glycol/t-BuOH (1:4) at the indicated magnifications of 5×, 10× and 20×, respectively.

Figure 12A:
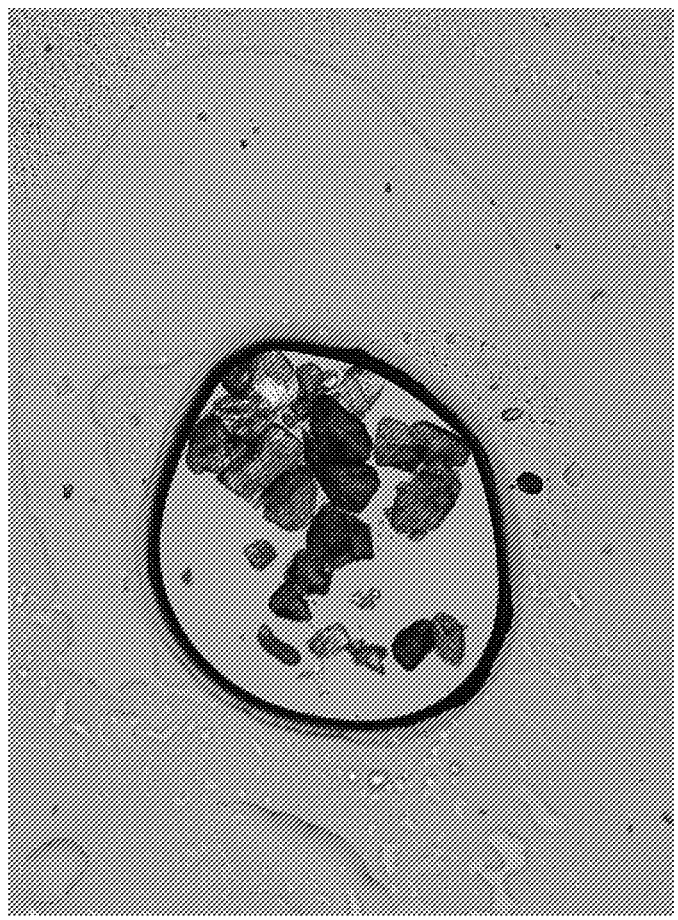
Figure 12B:
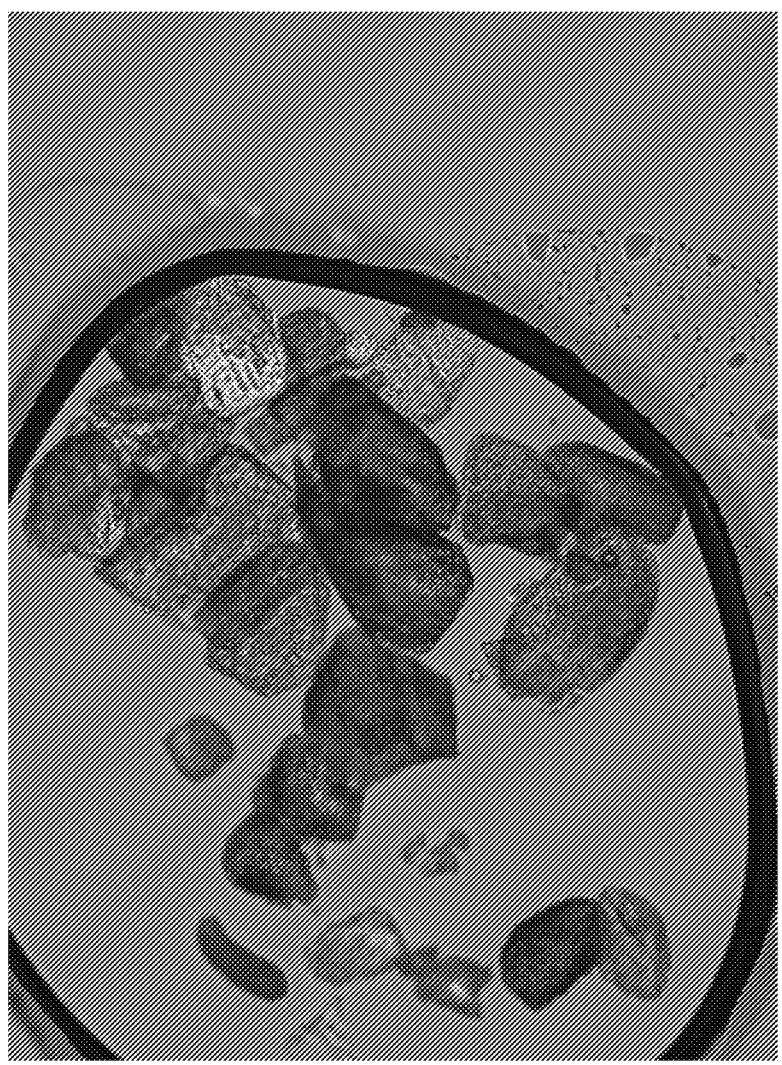
Figure 12C:
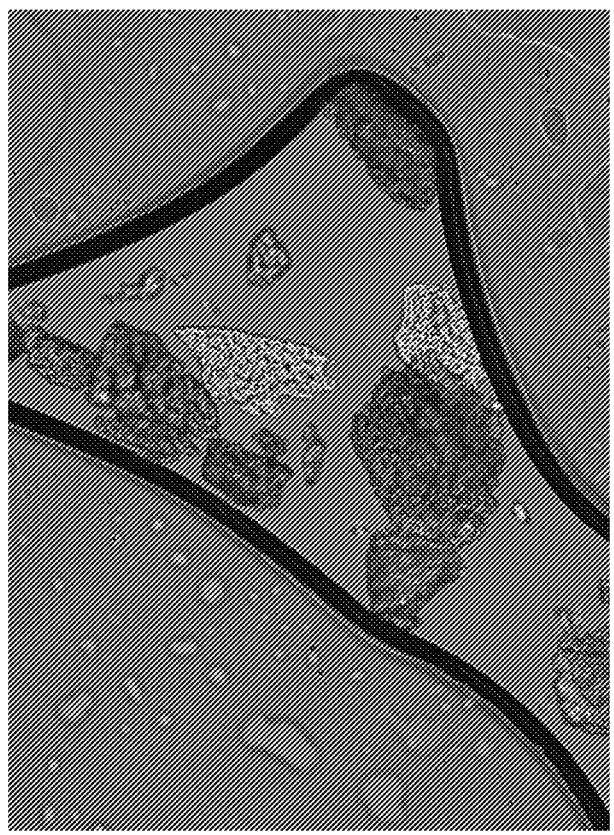

FIGS. 12A, 12B and 12C provides images of recrystallized HI-6 DMS from the single solvent system of propylene glycol (1,2-propane diol) at the indicated magnifications of 5×, 10× and 20×, respectively. A relatively small amount of t-BuOH was utilized to promote crystallization.

Figure 13A:
Figure 13B:
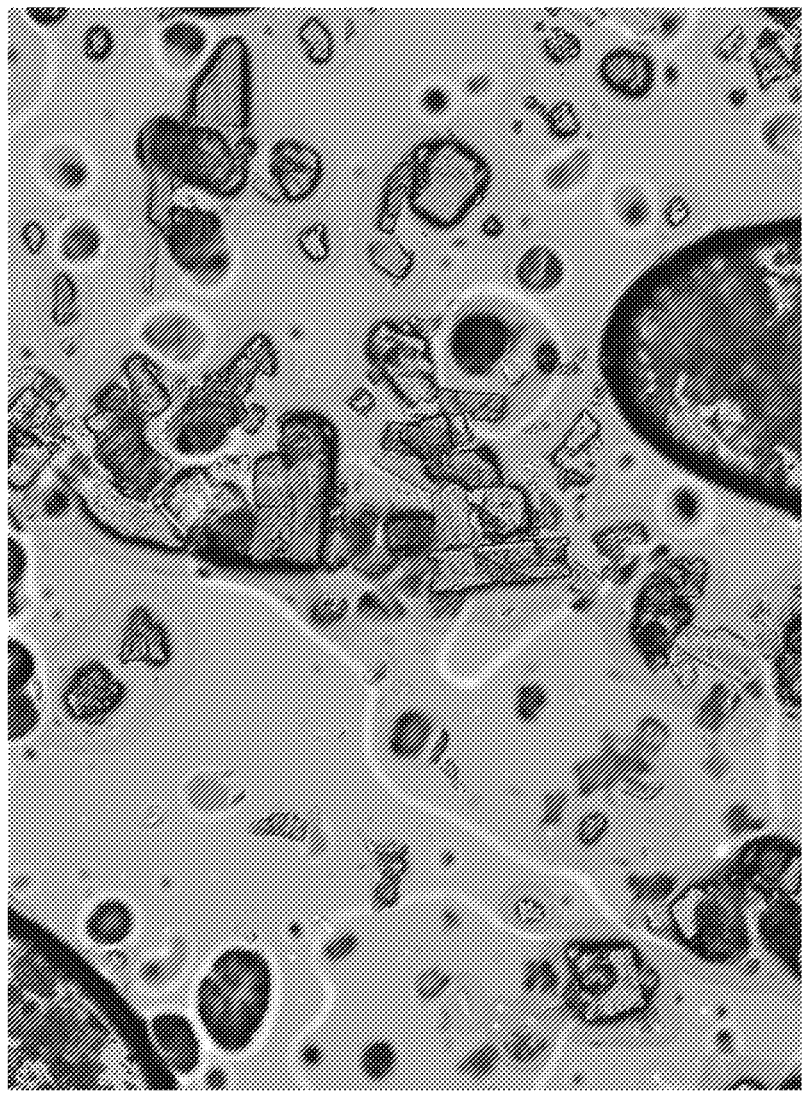
Figure 13C:
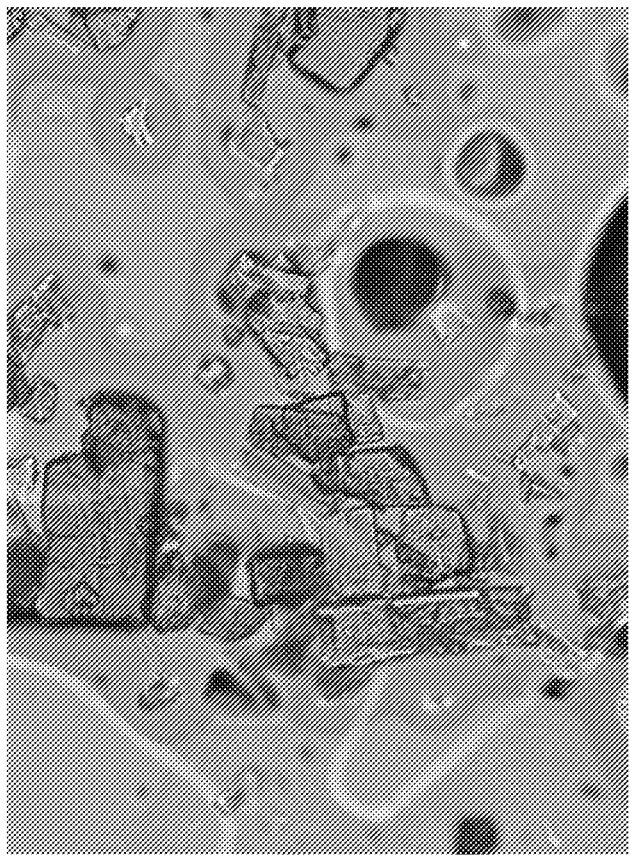

FIGS. 13A, 13B and 13C provide images of recrystallized HI-6 DMS from the binary solvent system of propylene glycol/DME (1:9) at the indicated magnifications of 5×, 10× and 20×, respectively.

Figure 14A:
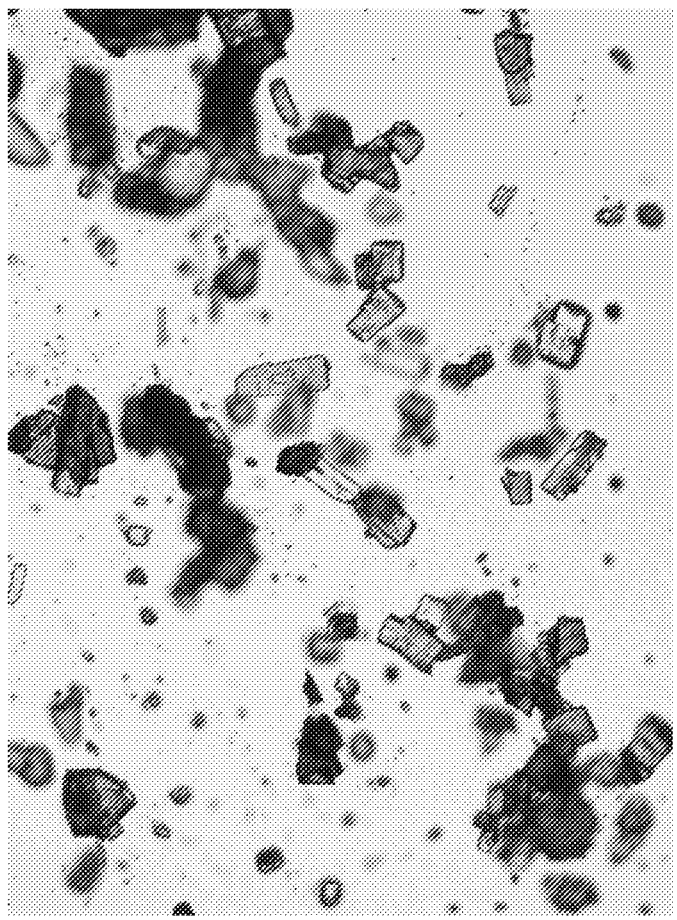
Figure 14B:
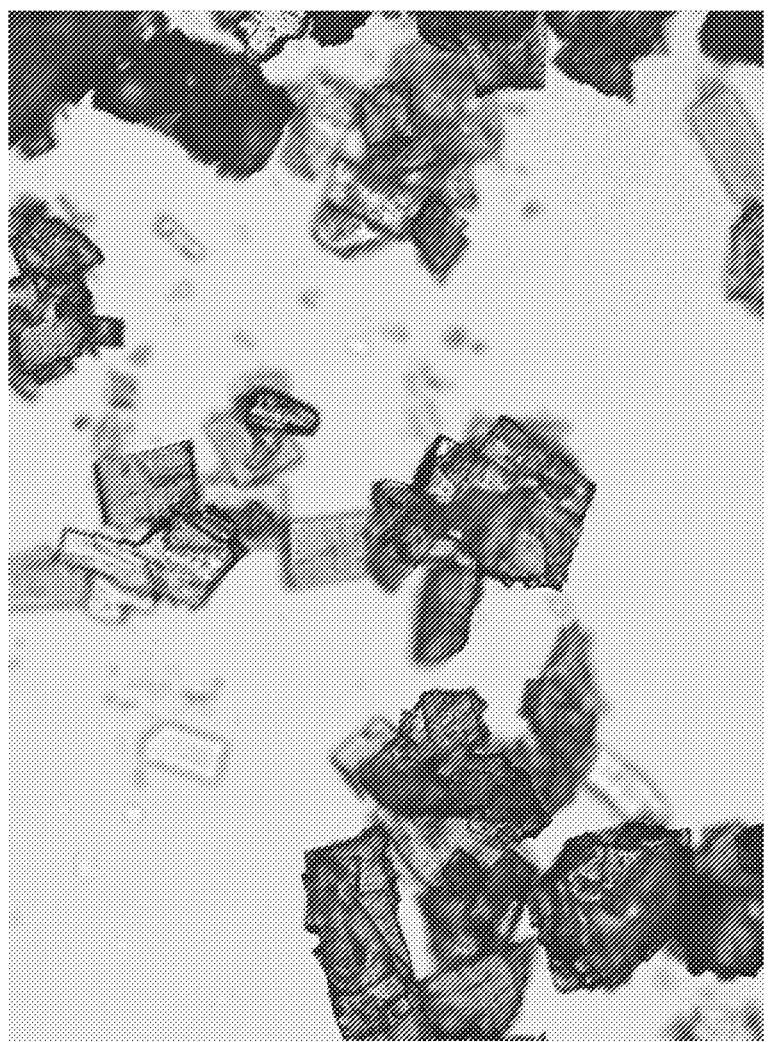
Figure 14C:
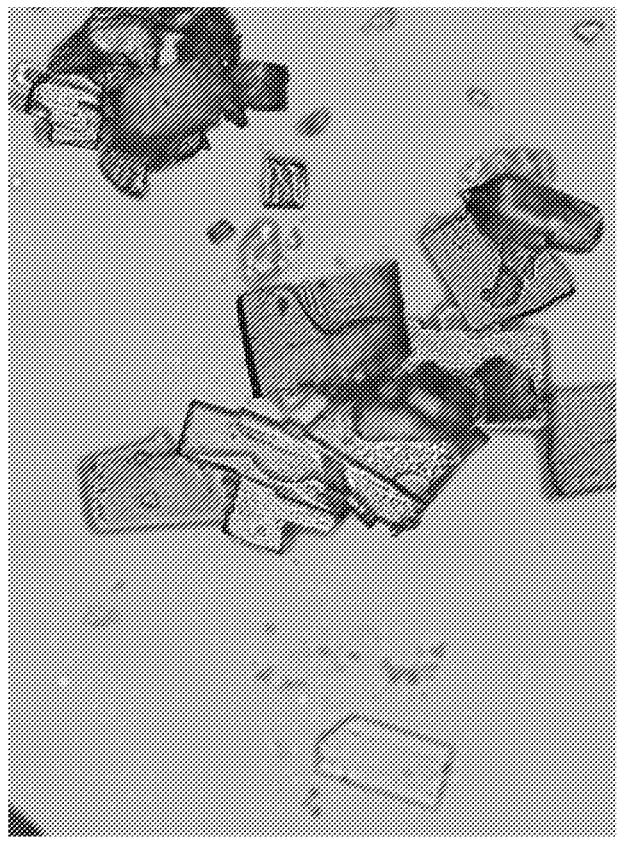

FIGS. 14A, 14B and 14C provide images of recrystallized HI-6 DMS from the binary solvent system of propylene glycol/EtOH (1:5) at the indicated magnifications of 5×, 10× and 20×, respectively.

Figure 15A:
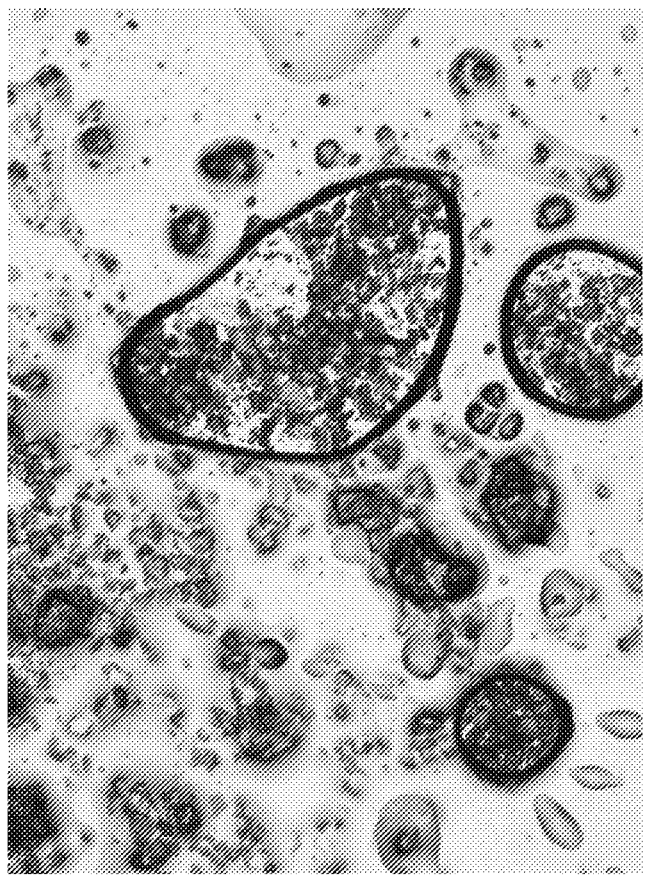
Figure 15B:
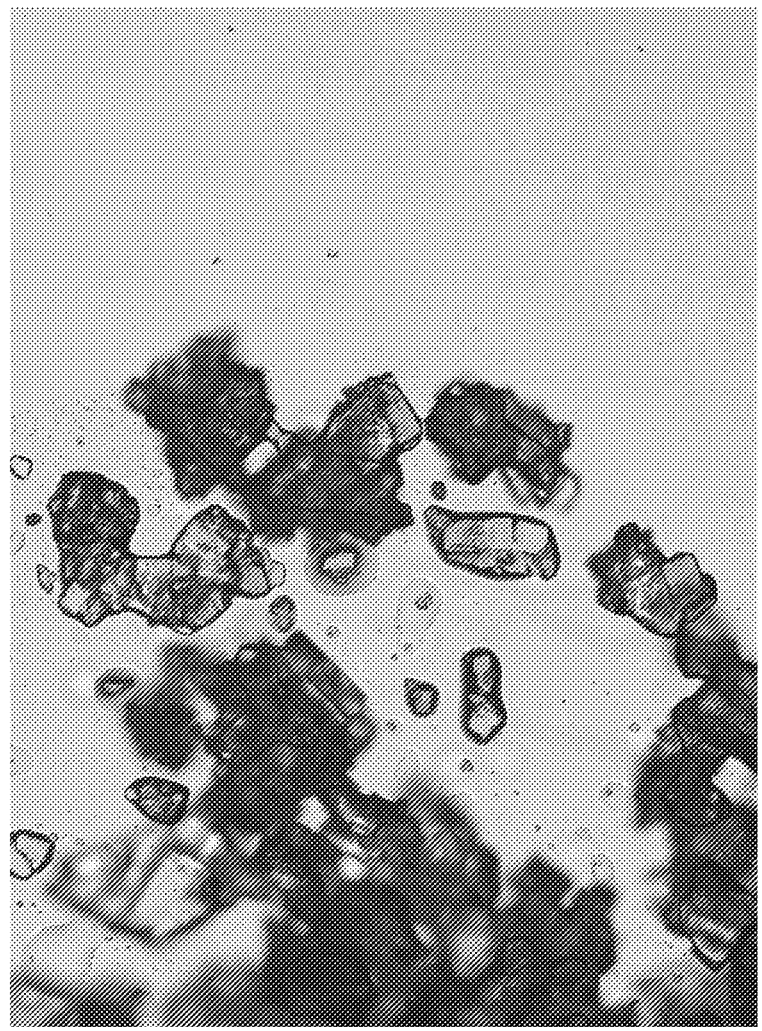
Figure 15C:
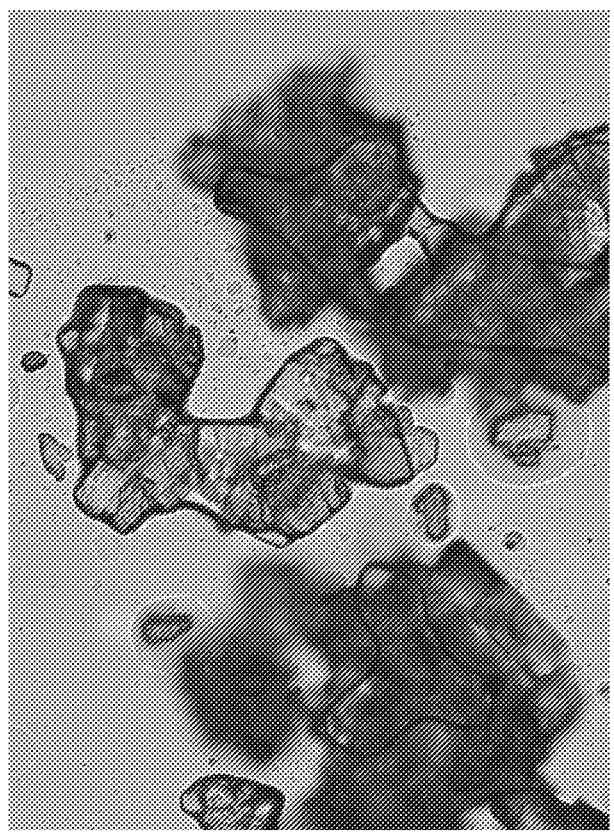

FIGS. 15A, 15B and 15C provide images of recrystallized HI-6 DMS from the binary solvent system of propylene glycol/MeCN (1:5) at the indicated magnifications of 5×, 10× and 20×, respectively.

Figure 16A:
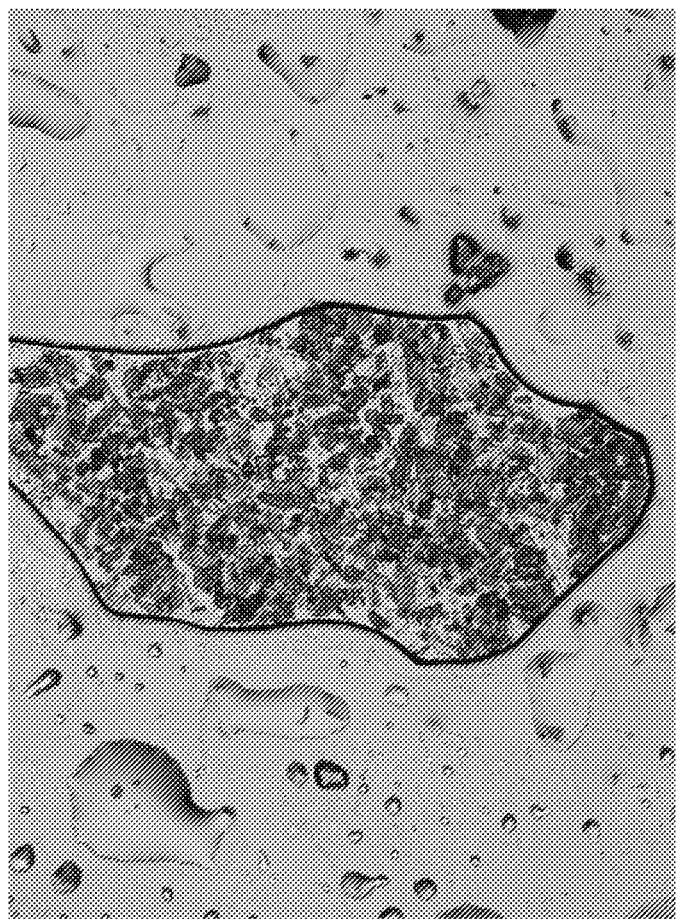
Figure 16B:
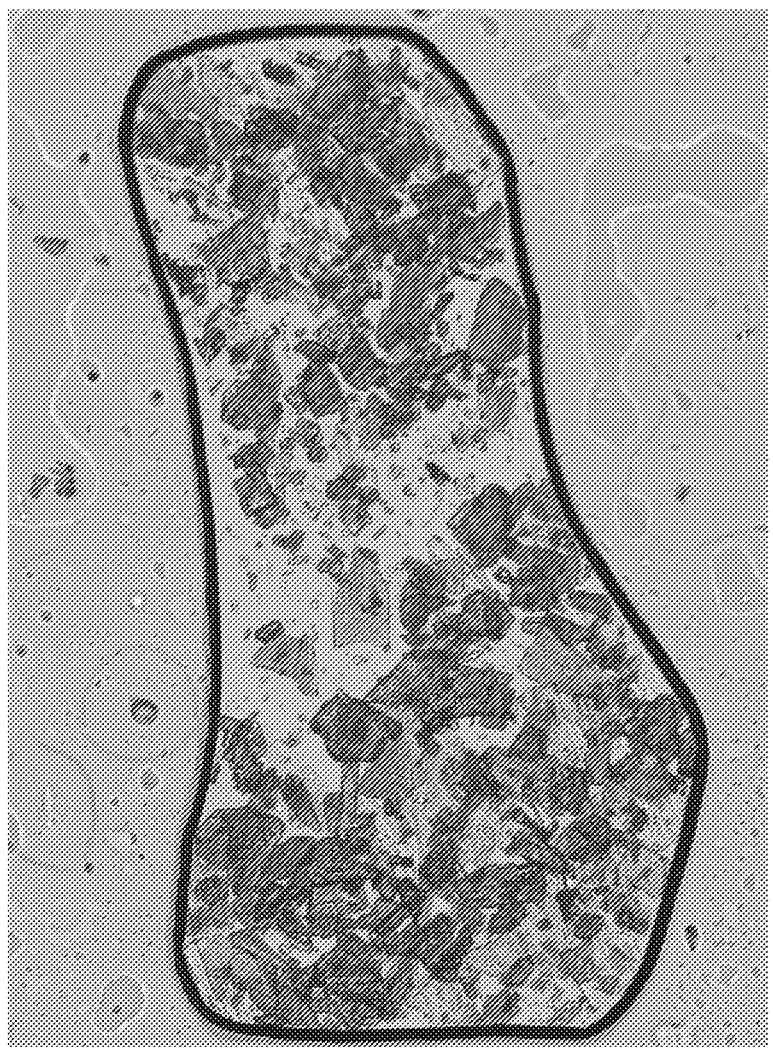
Figure 16C:

FIGS. 16A, 16B and 16C provide images of recrystallized HI-6 DMS from the binary solvent system of propylene glycol/tBuOH (1:2) at the indicated magnifications of 5×, 10× and 20×, respectively.

Figure 17A:
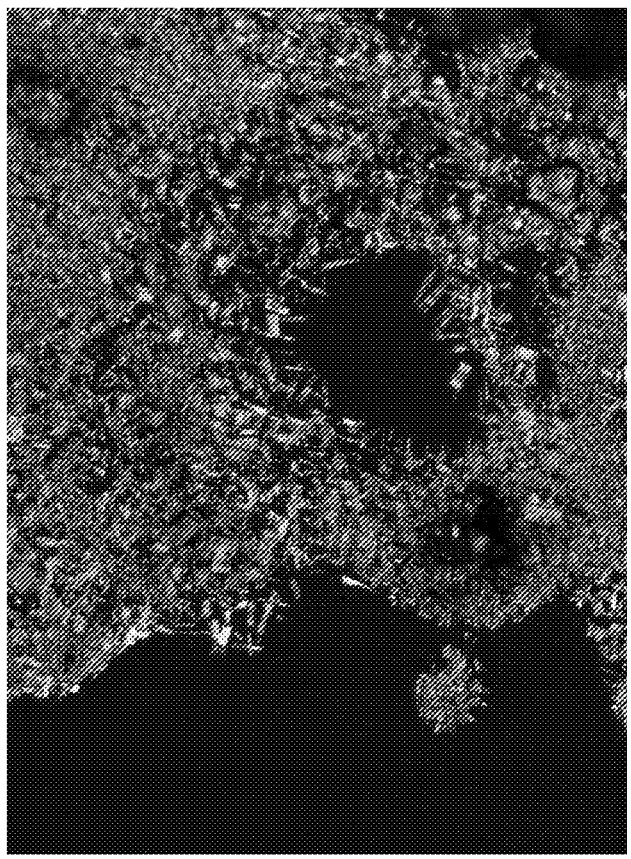
Figure 17B:
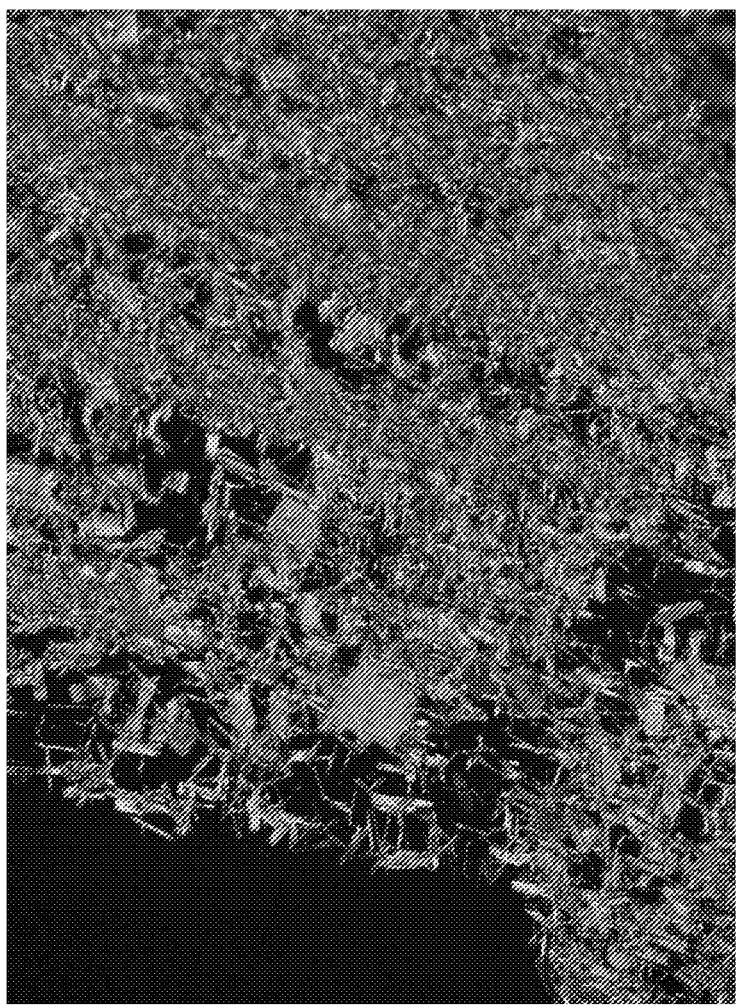
Figure 17C:

FIGS. 17A, 17B and 17C provide images of recrystallized HI-6 DMS from the single solvent system of water at the indicated magnifications of 5×, 10× and 20×, respectively.

Figure 18A:
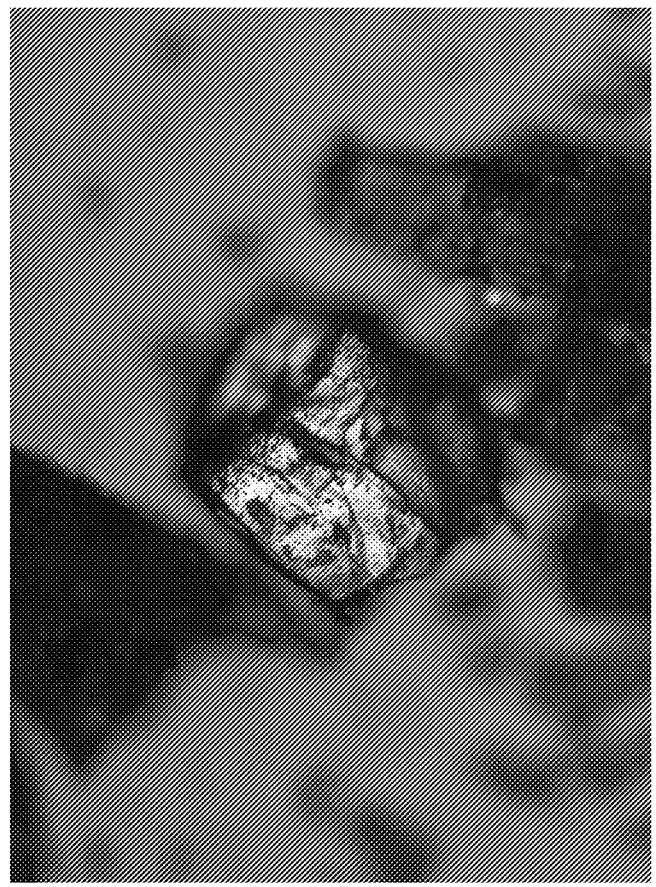
Figure 18B:
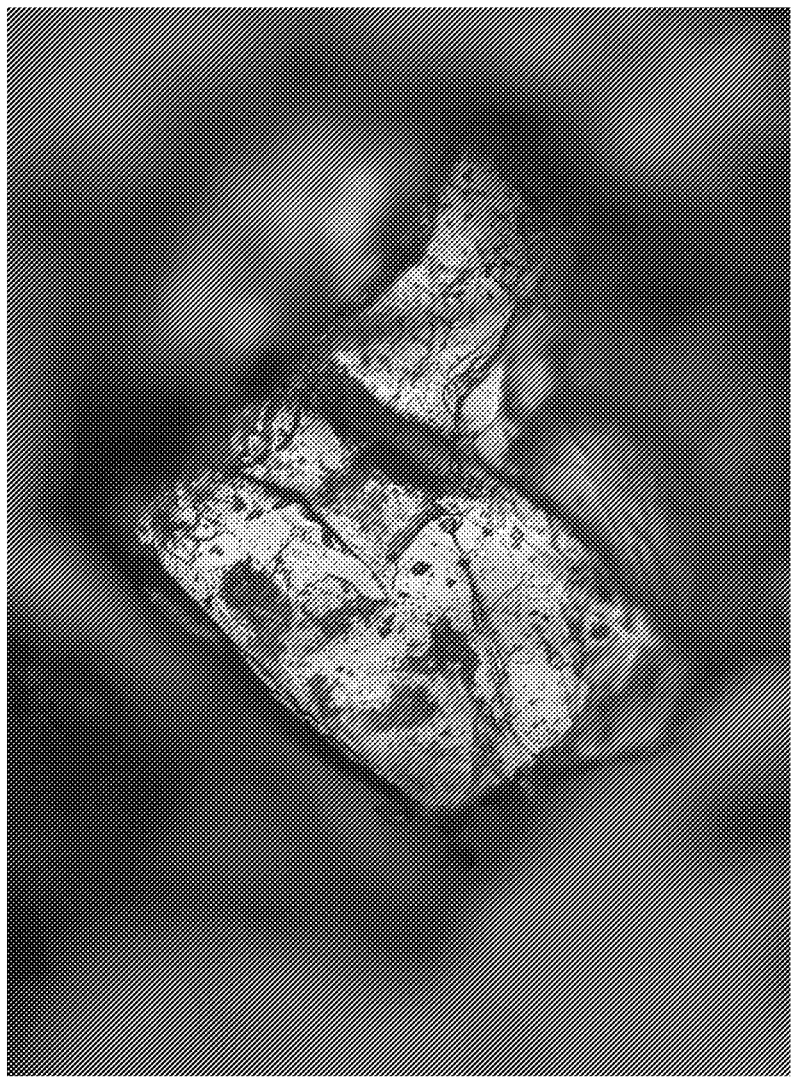
Figure 18C:
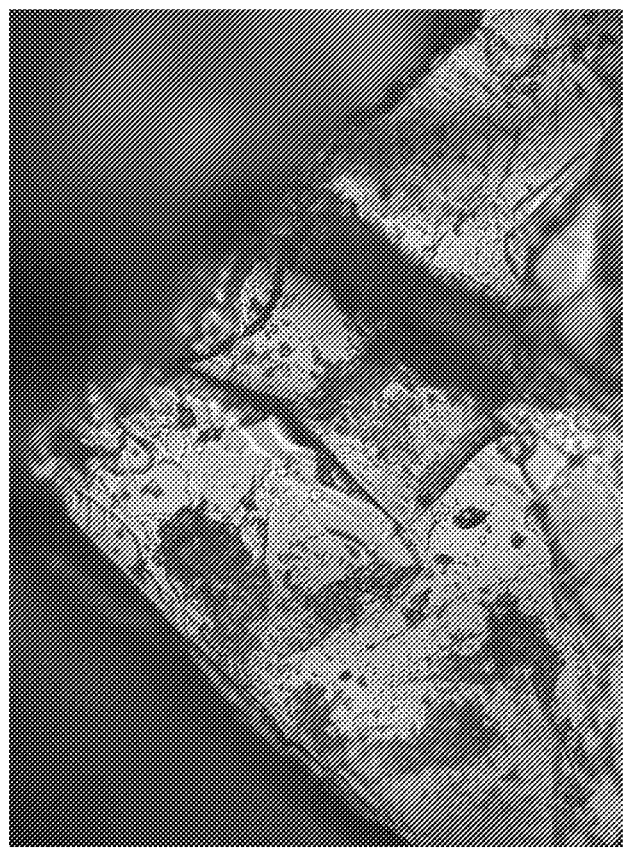

FIGS. 18A, 18B and 18C provide images of recrystallized HI-6 DMS from the binary solvent system of water/EtOH (1:14) at the indicated magnifications of 5×, 10× and 20×, respectively.

Figure 19A:
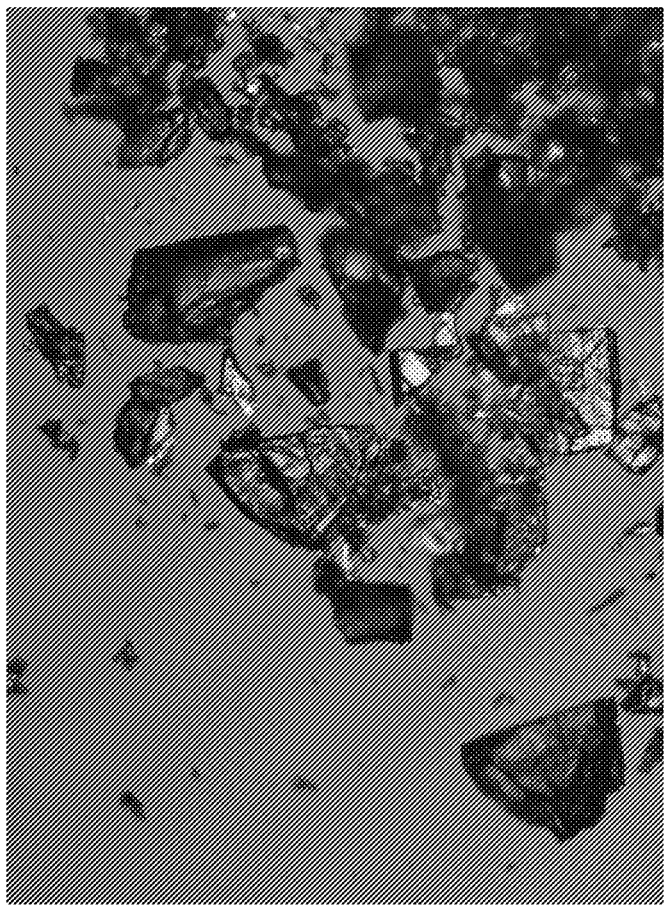
Figure 19B:
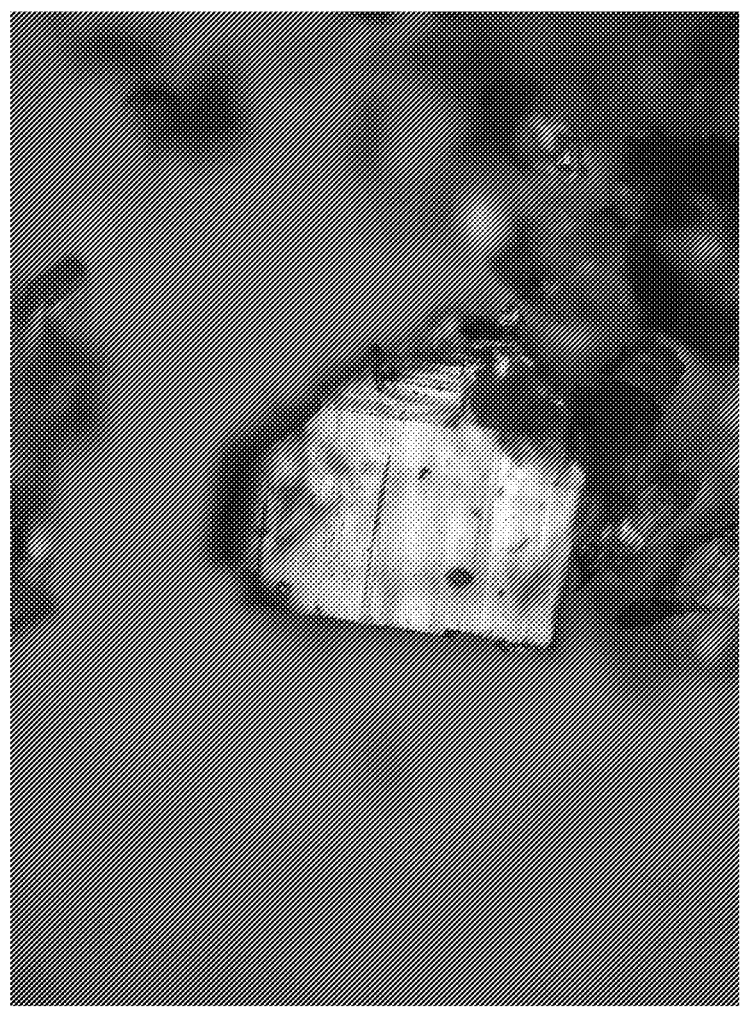
Figure 19C:
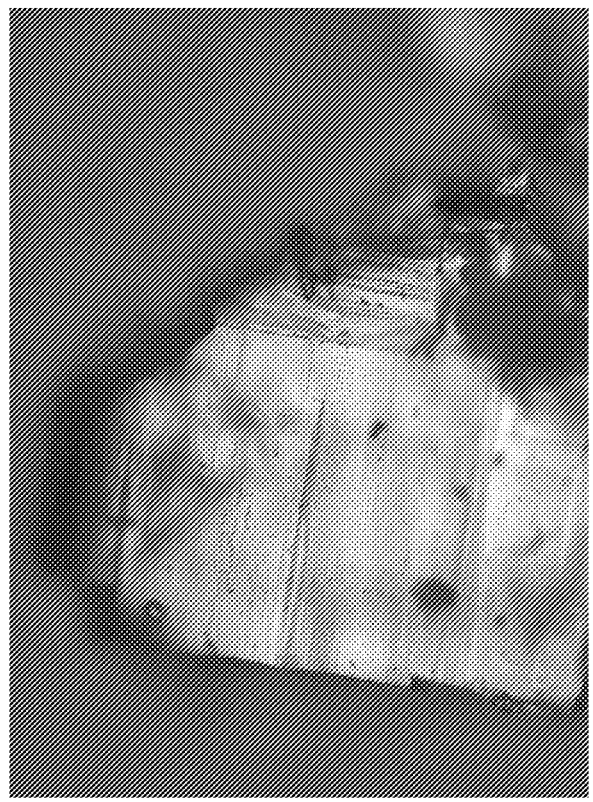

FIGS. 19A, 19B and 19C provide images of recrystallized HI-6 DMS from the binary solvent system of water/DMF (1:23) at the indicated magnifications of 5×, 10× and 20×, respectively.

Samples of the various recrystallized HI-6 DMS were then placed in a weighing dish and left out at ambient temperature (18° C. to 30° C.) and ambient humidity (50% to 60%) to evaluate moisture uptake. The results are provided in Table 6:

also steadily lost weight under ambient temperature (~25° C.) and humidity conditions (~50-60% relative humidity). It may therefore be appreciated that such result is of significant benefit from the perspective that the goal herein was to provide HI-6 DMS with the characteristic that it would then show relatively lower hydroscopic performance. That is, relatively low levels of water absorption, or even resistance to water absorption, to improve their shelf life stability and better maintain their performance as an OPNA reactivator when maintained in storage prior to use within an injectable formulation, such as in an autoinjector.

Experimental

General Procedure for Solubility Determination

Solvent was added to relatively small (~100 mg) amounts of HI-6 DMS in a 20 mL vial and adding and heated on a hot plate to effect dissolution, then allowed to cool to room temperature. This process was repeated until either most of the HI-6 DMS was solubilized after the heat-cool cycle, or 20 mL of solvent was reached. When most of the solids were dissolved, the saturated solution was filtered, the solution was weighed and the solvent removed under reduced pressure. The weight of HI-6 DMS recovered divided by the weight of the solvent added determined the solubility. See Table 1.

TABLE 6

Moisture Uptake of Recrystallized HI-6 From Identified Solvent-Antisolvent Systems

| Solvent | Anti solvent | Day | | | | | | | | Ave mg/day (%) |
| --- | --- | --- | --- | --- | --- | --- | --- | --- | --- | --- |
| | | 0 | 1 | 2 | 3 | 4 | 5 | 6 | 7 | |
| Methanol | DMF | 9.3 | 8.9 | | 9.1 | 8.9 | 8.9 | 8.6 | 8.6 | −1.429 |
| | tBuOH | 6.2 | 6.5 | | 6.3 | 6.5 | 6.4 | 6.6 | 6.6 | 1.111 |
| | EtOH | 9.4 | 10 | | 9.5 | 9.6 | 9.5 | 9.9 | 10 | 1.368 |
| | DME | 6.8 | 6.8 | | 6.7 | 6.8 | 6.7 | 7.1 | 6.9 | 1.045 |
| | MeCN | 5.3 | 4.4 | | 4.4 | 4.6 | 4.5 | 4.6 | 4.7 | 1.364 |
| | N/A | 17.2 | 16.6 | 16.2 | 16.3 | 16.7 | 16.6 | | | 0.988 |
| Ethylene Glycol | tBuOH | 17.2 | 15.9 | | 15.4 | 15.4 | 15.4 | 15.4 | 15.2 | −0.26 |
| | EtOH | 8.2 | 8 | | 8.1 | 8.2 | 8.3 | 8.4 | 8.3 | 0.741 |
| | MeCN | 7 | 6.9 | | 6.9 | 7 | 7.1 | 7.2 | 7.1 | 0.87 |
| | N/A | 10.5 | 10.7 | 10.6 | 10.3 | 10.7 | 10.4 | | | −0.216 |
| 1,2-propane diol | tBuOH | 19.2 | 15.9 | | 12.7 | 13 | 12.8 | 12.7 | 12.7 | −0.236 |
| | DME | 10.2 | 8.1 | | 7.9 | 8.2 | 8 | 8.2 | 8.3 | 1.013 |
| | MeCN | 5.3 | 4.5 | | 4.6 | 4.7 | 4.9 | 4.9 | 4.9 | 1.739 |
| | EtOH | 7.5 | 6.6 | | 6.7 | 6.6 | 6.7 | 6.8 | 6.7 | 0.299 |
| | N/A | 5.2 | 5.2 | 5.4 | 5.1 | 5.4 | 5.2 | | | 0.159 |
| | | Sample wt (mg) | | | | | | | | |

As noted above, reference to "N/A" in the column marked "Antisolvent", in the case of ethylene glycol and 1,2-propane diol, is reference to the fact that such solvents were utilized on their own to dissolve HI-6 DMS, which solutions were then concentrated providing an oil, which upon treatment of a relatively small amount of tert-butanol, led to recrystallization.

As can be seen from Table 6, the samples underwent some initial loss in weight, which is attributed to residual solvent loss. As can therefore now be seen, when forming by dissolving HI-6 DMS in ethylene glycol and then utilizing tBuOH as the antisolvent, one provides a recrystallized HI-6 DMS that steadily lost weight under ambient temperature and ambient humidity conditions. Similarly, by dissolving HI-6 DMS in 1,2-propane diol and then utilizing tBuOH as the antisolvent, one provides a recrystallized HI-6 DMS that General Procedure for Binary Solvent System Evaluation For the moderately soluble solvents (MeOH, 1,2-propane diol), 1 mL was added to relatively small (~50 mg) amounts of HI-6 DMS and heated to effect dissolution and was allowed to cool to room temperature. Antisolvent was then added until the mixture become cloudy and solvents precipitated. The mixture was then heated until a homogeneous solution was achieved, then allowed to cool to room temperature and allowed to crystalize. If only relatively small amounts of crystals formed, more antisolvent was added and the process repeated. For the relatively highly soluble solvents (ethylene glycol, water) the process was done in reverse: where antisolvent was added first and small amounts of the solvent were added. See Tables 1 and 2.

General Procedure for Recrystallization

For the single solvent recrystallization conditions, HI-6 DMS (~100 mg) was dissolved in the appropriate solvent according to the maximum solubilities as determined in peak at 6.36 ppm ($CH_2$) was chosen as the reference peak for HI-6 DMS and the relative ratios between the crystallization solvents and water (3.37 ppm) was determined. The solvate ratios were determined by normalizing the peak integrations by the number of protons to get the molar ratios, then rounding to the nearest half mol fraction. The results are listed in Table 7.

TABLE 7

| Solvent (A) | Antisolvent (B) | HI-6:A | HI-6:B | HI-6:$H_2O$ | Prediction |
|---|---|---|---|---|---|
| MeOH | N/A | | | | |
| | tBuOH | N/A | N/A | 1:3.11 | HI-6•3 $H_2O$ |
| | DME | N/A | N/A | 1:3.13 | HI-6•3 $H_2O$ |
| | EtOH | N/A | N/A | 1:3.20 | HI-6•3 $H_2O$ |
| | DMF | N/A | N/A | 1:3.03 | HI-6•3 $H_2O$ |
| | DMF$^a$ | N/A | N/A | 1:2.71 | HI-6•2.5 $H_2O$ |
| | MeCN | 1:0.95 | 1:0.64 | 1:5.13 | HI-6•1 MeOH•0.5 MeCN•5 $H_2O$ |
| ethylene glycol | N/A | | | | |
| | EtOH | 1:1.13 | 1:4.47 | 1:4.70 | HI-6•1 ethylene glycol•4.5 EtOH•4.5 $H_2O$ |
| | MeCN | 1:0.38 | N/A | 1:2.38 | HI-6•0.5 ethylene glycol•2.5 $H_2O$ |
| | tBuOH | 1:0.42 | N/A | 1:4.72 | HI-6•0.5 ethylene glycol•4.5 $H_2O$ |
| | tBuOH$^a$ | 1:0.06 | N/A | 1:1.13 | HI-6•1 $H_2O$ |
| 1,2-propane diol | N/A | | | | |
| | DME | 1:2.64 | N/A | 1:4.07 | HI-6•2.5 1,2-propane diol•4 $H_2O$ |
| | EtOH | 1:0.56 | N/A | 1:1.40 | HI-6•0.5 1,2-propane diol•1.5 $H_2O$ |
| | Me CN | 1:0.58 | N/A | 1:1.98 | HI-6•0.5 1,2-propane diol•2 $H_2O$ |
| | tBuOH | 1:0.62 | 1:5.27 | 1:2.14 | HI-6•0.5 1,2-propane diol•5 tBuOH•2 $H_2O$ |
| | tBuOH$^a$ | N/A | N/A | 1:1.79 | HI-6•1.5 $H_2O$ |
| $H_2O$ | N/A | N/A | N/A | 1:1.72 | HI-6•1.5 $H_2O$ |
| | EtOH | N/A | N/A | 1:0.87 | HI-6•1 $H_2O$ |
| | DMF | N/A | N/A | 1:1.63 | HI-6•1.5 $H_2O$ |
| HI-6 unprocessed | N/A | N/A | N/A | 1:1.13 | HI-6•1 $H_2O$ |

Table 1. The solutions were then concentrated under vacuum until precipitate was observed. The mixture was then heated and then allowed to cool to room temperature to produce HI-6 DMS crystals. For ethylene glycol and 1,2-propane diol, no crystals formed upon concentration and instead produced oils. These oils were titrated with ~1 mL tBuOH, at room temperature, which causes crystals of HI-6 DMS to form.

Two procedures were used to determine the binary solvent recrystallization conditions. For the relatively lower solubilizing solvents MeOH and 1,2-propane diol, a sample of HI-6 DMS (~100 mg) was dissolved in those solvents and the chosen anti-solvent was added until the mixture become cloudy. The mixture was then heated and then allowed to cool to room temperature. The process was repeated until ~50% of the HI-6 DMS had recrystalized. For the relatively higher solubilizing solvents ethylene glycol and water, a sample of HI-6 DMS (~100 mg) was slurried in the anti-solvent of choice and small amounts of the solubilizing solvent was added. The mixture was then heated and then allowed to cool to room temperature. The process was repeated until most of the HI-6 DMS dissolved upon heating. See Table 3.

Analysis By NMR

An authentic sample of HI-6 DMS was dissolved in deuterated dimethyl sulfoxide (DMSO-$D^6$) and a $^1$H-NMR spectrum was obtained. All peaks were assigned and the spectrum was used as the baseline to determine how much water and solvents were present in the samples. Samples (~10 mg) of the of the HI-6 DMS crystals were dried in a vacuum overnight and dissolved in deuterated dimethyl sulfoxide (DMSO-$D^6$) fresh from an ampule to minimize adventitious water. $^1$H-NMR spectrums were taken and the Most samples from the MeOH series seemed to produce trihydrates, the sample in MeCN however contained both MeOH and MeCN. In contrast to this, the ethylene glycol and 1,2-propane diol samples all contained solvent. The samples crystalized from water contained less water than those obtained from other solvents, estimating at either mono or sesquihydrates. During a subsequent deliquescent test, some samples showed continued weight loss during the seven day experiment, namely the MeOH/DMF, ethylene glycol/tBuOH and 1,2-propane diol/tBuOH samples. These samples were analyzed by NMR after the test to see how the ratios between water and residual solvents changed. Surprisingly, the residual solvent disappeared and the overall water content decreased to the ratios obtained with the water crystallizations.

Analysis by X-Ray Powder Diffraction

Figure 20:
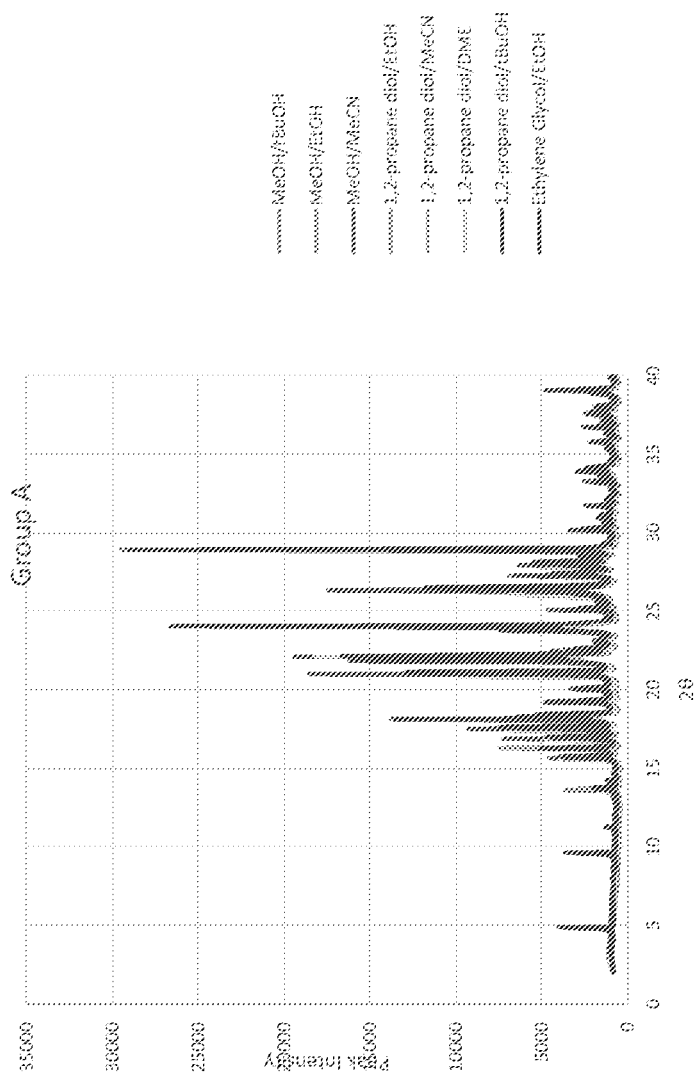
FIG. 20 illustrates an XRD overlay of the identified Group A sample.
Figure 21:
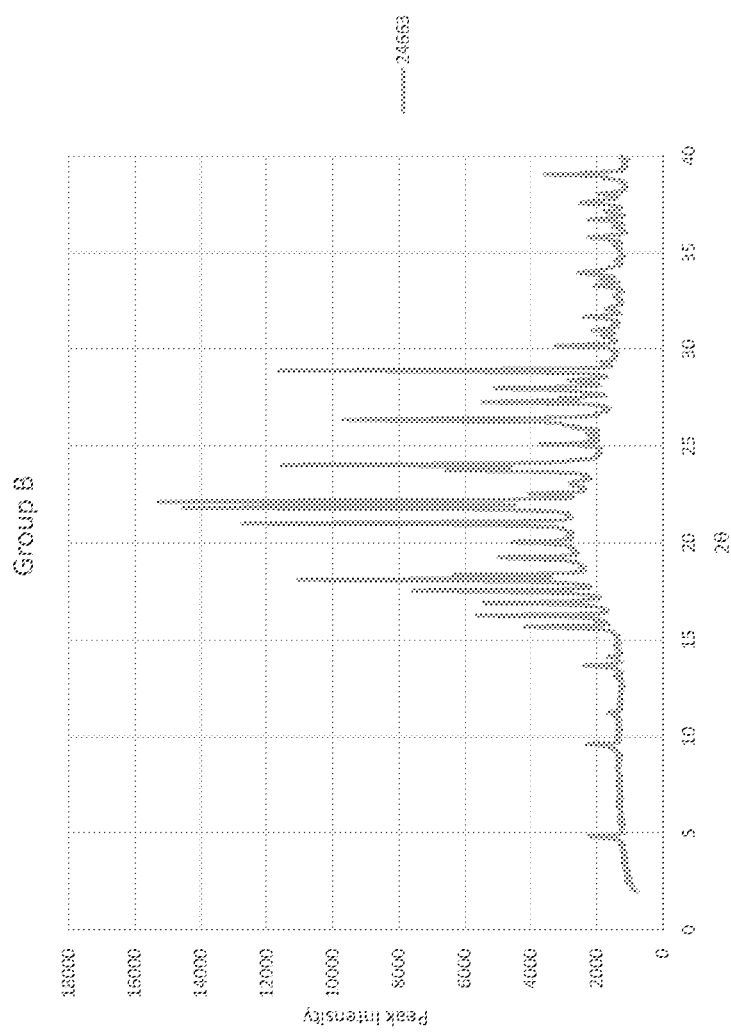
FIG. 21 illustrates an XRD overlay of the identified Group B sample.
Figure 22:
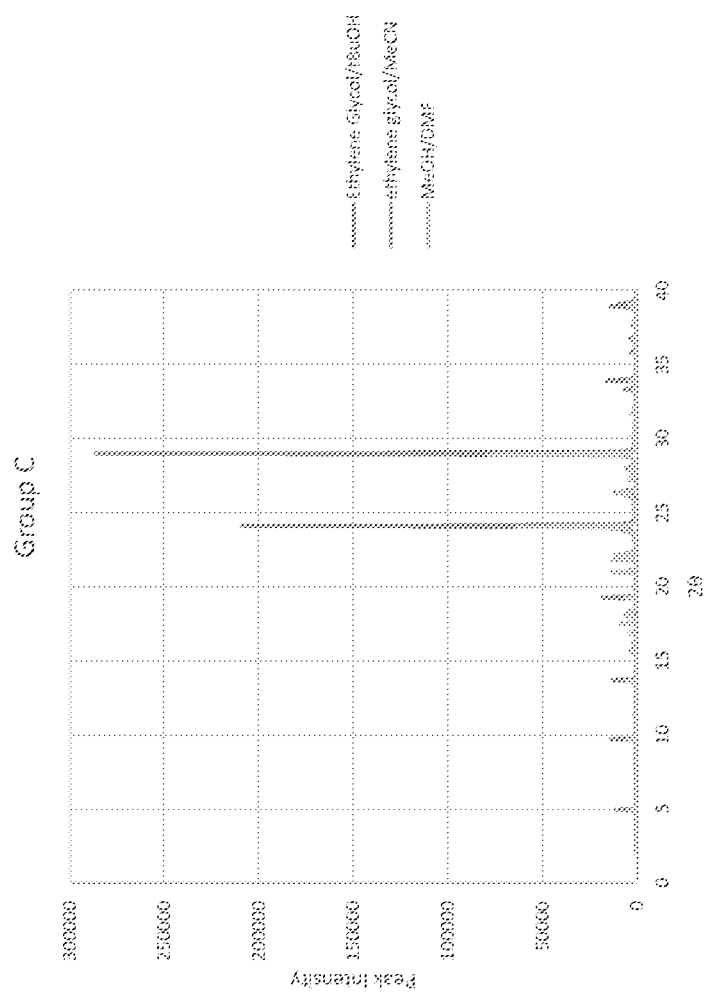
FIG. 22 illustrates an XRD overlay of the identified Group C sample.

Samples of each binary solvent crystallization were sent to Triclinic Labs for analysis by x-ray powder diffraction. The fourteen samples were visually separated into three groups: A) crystalline samples with a number of discrete diffraction peaks across the range of measured 2θ, B) a sample with a broad baseline indicating amorphous character and C) a crystalline sample with peaks of relatively strong intensity at 24.04 θ and 28.92 θ. An overlay of group A can be found in FIG. 20, an overlay of Group B can be found in FIG. 21 and an overlay of Group C can be found in FIG. 22. MeOH/DMF, ethylene glycol/MeCN and ethylene glycol/tBuOH all belonged to group C, methanol/DME belonged to group B and all the rest belonged to group A. The intense peaks in group C are most likely caused by the crystals having a preferred orientation (PO) during the X-ray analysis. The PO in these patterns occurs because one or more crystal faces in the samples are preferentially interrogated by the x-ray beam due to alignment of the crystals in the holder. When looking at the X-ray data by solvent, is seems that ethylene glycol seems to produce crystals with the preferred orientation. Using the unique 2θ values, the unit crystal structure was calculated for each sample. A solution was found for each sample except for MeOH/DME due to the presence of the amorphous phase. Confirming the results of the overlay, all crystals appeared to be orthorhombic, with the space group Pcab and similar unit cell dimensions (Table 8).

TABLE 8

| Solvent | Antisolvent | symmetry | spacegroup | Crystal Dimentions | | | |
|---|---|---|---|---|---|---|---|
| | | | | a (Å) | b (Å) | c (Å) | V (Å^3) |
| MeOH | tBuOH | orthorhombic | Pcab | 37.17 | 16.228 | 6.969 | 4203.664 |
| | EtOH | orthorhombic | Pcab | 37.218 | 16.246 | 6.98 | 4220.413 |
| | DME | orthorhombic | Pcab | — | — | — | — |
| | DMF | orthorhombic | Pcab | 37.137 | 16.243 | 6.976 | 4208.037 |
| | MeCN | orthorhombic | Pcab | 37.17 | 16.228 | 6.969 | 4203.664 |
| 1,2-propane diol | EtOH | orthorhombic | Pcab | 37.171 | 16.245 | 6.986 | 4218.446 |
| | MeCN | orthorhombic | Pcab | 37.138 | 16.252 | 6.975 | 4209.878 |
| | DME | orthorhombic | Pcab | 37.144 | 16.305 | 7.033 | 4259.416 |
| | tBuOH | orthorhombic | Pcab | 37.194 | 16.193 | 6.947 | 4184.056 |
| Ethylene Glycol | EtOH | orthorhombic | Pcab | 37.138 | 16.252 | 6.975 | 4209.878 |
| | tBuOH | orthorhombic | Pcab | 37.188 | 16.277 | 6.983 | 4226.873 |
| | MeCN | orthorhombic | Pcab | 37.159 | 16.309 | 6.97 | 4224.002 |
| Water | EtOH | orthorhombic | Pcab | 37.17 | 16.228 | 6.969 | 4203.664 |
| | DMF | orthorhombic | Pcab | 37.301 | 16.233 | 6.973 | 4222.201 |

While the invention has been particularly shown and described with reference to the various exemplary embodiments herein, it will be understood by those of skill in the art that various changes in form may be made therein without departing from the scope of the invention encompassed by the appended claims.

What is claimed is:

1. A method for making a solvate and hydrate of (1-(2-(hydroxyiminomethyl)pyridinium)-3-(4-carbamoylpyridinium)-2-oxapropane) dimethanesulfonate comprising:
    dissolving (1-(2-(hydroxyiminomethyl)pyridinium)-3-(4-carbamoylpyridinium)-2-oxapropane) dimethanesulfonate in an alkyl-based glycol comprising ethylene glycol or 1,2-propane diol and adding an antisolvent comprising tert-butanol to make a solvate and hydrate of (1-(2-(hydroxyiminomethyl)pyridinium)-3-(4-carbamoylpyridinium-2-oxapropane) dimethanesulfonate wherein said solvate and hydrate of (1-(2-(hydroxyiminomethyl)pyridinium)-3-(4-carbamoylpyridinium)-2-oxapropane) does not absorb water over a seven-day period under ambient temperature and humidity conditions.

2. The method of claim 1 wherein the ratio of ethylene glycol to tert-butanol is 1:4.

3. The method of claim 1 wherein the ratio of propylene glycol to tert-butanol is 1:2.

4. The method of claim 1 wherein said recrystallized solvate and hydrate of (1-(2-(hydroxyiminomethyl)pyridinium)-3-(4-carbamoylpyridinium)-2-oxapropane) dimethanesulfonate from said ethylene glycol solvent and said antisolvent of tert-butanol indicates, following heating in a differential scanning calorimeter (DSC) at a heating rate of 10° C. per minute, a DSC melting point onset of 133° C., a DSC melting point of 140° C. and a DSC decomposition temperature of 146° C.

5. The method of claim 1 wherein said recrystallized solvate and hydrate of (1-(2-(hydroxyiminomethyl)pyridinium)-3-(4-carbamoylpyridinium)-2-oxapropane) dimethanesulfonate from said 1,2-propane diol solvent and said antisolvent of tert-butanol indicates, following heating in a differential scanning calorimeter (DSC) at a heating rate of 10° C. per minute, a DSC melting point onset of 142° C., a DSC melting point of 144° C. and a DSC decomposition temperature of 149° C.

* * * * *